(12) United States Patent
Parlikar et al.

(10) Patent No.: US 8,282,564 B2
(45) Date of Patent: Oct. 9, 2012

(54) SYSTEMS AND METHODS FOR MODEL-BASED ESTIMATION OF CARDIAC OUTPUT AND TOTAL PERIPHERAL RESISTANCE

(75) Inventors: Tushar A. Parlikar, Cambridge, MA (US); Gireeja V. Ranade, Berkeley, CA (US); Thomas Heldt, Cambridge, MA (US); George C. Verghese, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1135 days.

(21) Appl. No.: 12/121,042

(22) Filed: May 15, 2008

(65) Prior Publication Data

US 2008/0287812 A1 Nov. 20, 2008

Related U.S. Application Data

(60) Provisional application No. 60/938,253, filed on May 16, 2007.

(51) Int. Cl.
*A61B 5/02* (2006.01)
(52) U.S. Cl. ..................................................... 600/485
(58) Field of Classification Search .................. None
See application file for complete search history.

(56) References Cited

U.S. PATENT DOCUMENTS

| | | | |
|---|---|---|---|
| 4,236,527 A | 12/1980 | Newbower et al. | |
| 4,507,974 A | 4/1985 | Yelderman | |
| 5,146,414 A | 9/1992 | McKown et al. | |
| 5,153,178 A | 10/1992 | Maroko | |
| 5,400,793 A | 3/1995 | Wesseling | |
| 5,687,733 A | 11/1997 | McKown | |
| 6,485,431 B1 | 11/2002 | Campbell et al. | |
| 6,758,822 B2 | 7/2004 | Romano | |
| 2003/0040675 A1 | 2/2003 | Sharrock | |
| 2004/0158163 A1 | 8/2004 | Cohen et al. | |
| 2004/0249297 A1 | 12/2004 | Pfeiffer et al. | |
| 2004/0254483 A1 | 12/2004 | Zdeblick et al. | |
| 2005/0015009 A1 | 1/2005 | Mourad et al. | |
| 2005/0096557 A1 | 5/2005 | Vosburgh et al. | |
| 2005/0124903 A1 | 6/2005 | Roteliuk et al. | |
| 2005/0124904 A1 | 6/2005 | Roteliuk | |
| 2006/0008923 A1 | 1/2006 | Anderson et al. | |
| 2006/0178589 A1 | 8/2006 | Dobak | |
| 2006/0235323 A1 | 10/2006 | Hatib et al. | |
| 2007/0016031 A1 | 1/2007 | Mourad et al. | |
| 2007/0024946 A1 | 2/2007 | Panasyuk et al. | |
| 2007/0197921 A1* | 8/2007 | Cohen et al. ................... | 600/485 |
| 2008/0015451 A1 | 1/2008 | Hatib et al. | |
| 2008/0287753 A1 | 11/2008 | Parlikar et al. | |
| 2008/0294057 A1 | 11/2008 | Parlikar et al. | |
| 2009/0112113 A1 | 4/2009 | Mukkamala | |

FOREIGN PATENT DOCUMENTS

| | | |
|---|---|---|
| WO | WO-2007/109059 A2 | 9/2007 |
| WO | WO-2008/144490 A1 | 11/2008 |
| WO | WO-2008/144525 A1 | 11/2008 |

OTHER PUBLICATIONS

International Search Report for PCT/US08/63725 dated Sep. 26, 2008, 2 pages.
Written Opinion of the International Searching Authority for PCT/US08/63725 dated Sep. 26, 2008, 6 pages.
International Preliminary Report on Patentability and Written Opinion for International Application No. PCT/US2008/063725 dated Nov. 26, 2009.
Cheatham et al., "Shock: An Overview," Orlando Regional Medical Center, 2004, available online at http://www.surgicalcriticalcare.net/Lectures/shock_overview.pdf.
International Preliminary Report on Patentability and Written Opinion for International Application No. PCT/US2008/0638725 dated Nov. 26, 2009.
International Preliminary Report on Patentability and Written Opinion for International Application No. PCT/US2008/063915 dated Nov. 26, 2009.
International Search Report and Written Opinion of the International Searching Authority for International Application No. PCT/US08/638725 dated Sep. 26, 2008.
International Search Report and Written Opinion of the International Searching Authority for International Application No. PCT/US08/63915 dated Oct. 3, 2008.
Parlikar et. al., "Cycle-Averaged Models of Cardiovascular Dynamics," IEEE Trans. On Circuits and Systems—1, vol. 53, No. 11, pp. 2459-2468, Nov. 2006.
Parlikar et. al., "Model-based estimation of cardiac output and total peripheral resistance," Computer in Cardiology, vol. 34 (2007), pp. 379-382.

* cited by examiner

*Primary Examiner* — Tracy Vivlemore
(74) *Attorney, Agent, or Firm* — Ropes & Gray LLP

(57) ABSTRACT

The methods and systems for estimating cardiac output and total peripheral resistance include observing arterial blood pressure waveforms to determine intra-beat and inter-beat variability in arterial blood pressure and estimating from the variability a time constant for a lumped parameter beat-to-beat averaged Windkessel model of the arterial tree. Uncalibrated cardiac output and uncalibrated total peripheral resistance may then be calculated from the time constant. Calibrated cardiac output and calibrated total peripheral resistance may be computed using calibration data, assuming an arterial compliance that is either constant or dependent on mean arterial blood pressure. The parameters of the arterial compliance may be estimated in a least-squares manner.

62 Claims, 13 Drawing Sheets

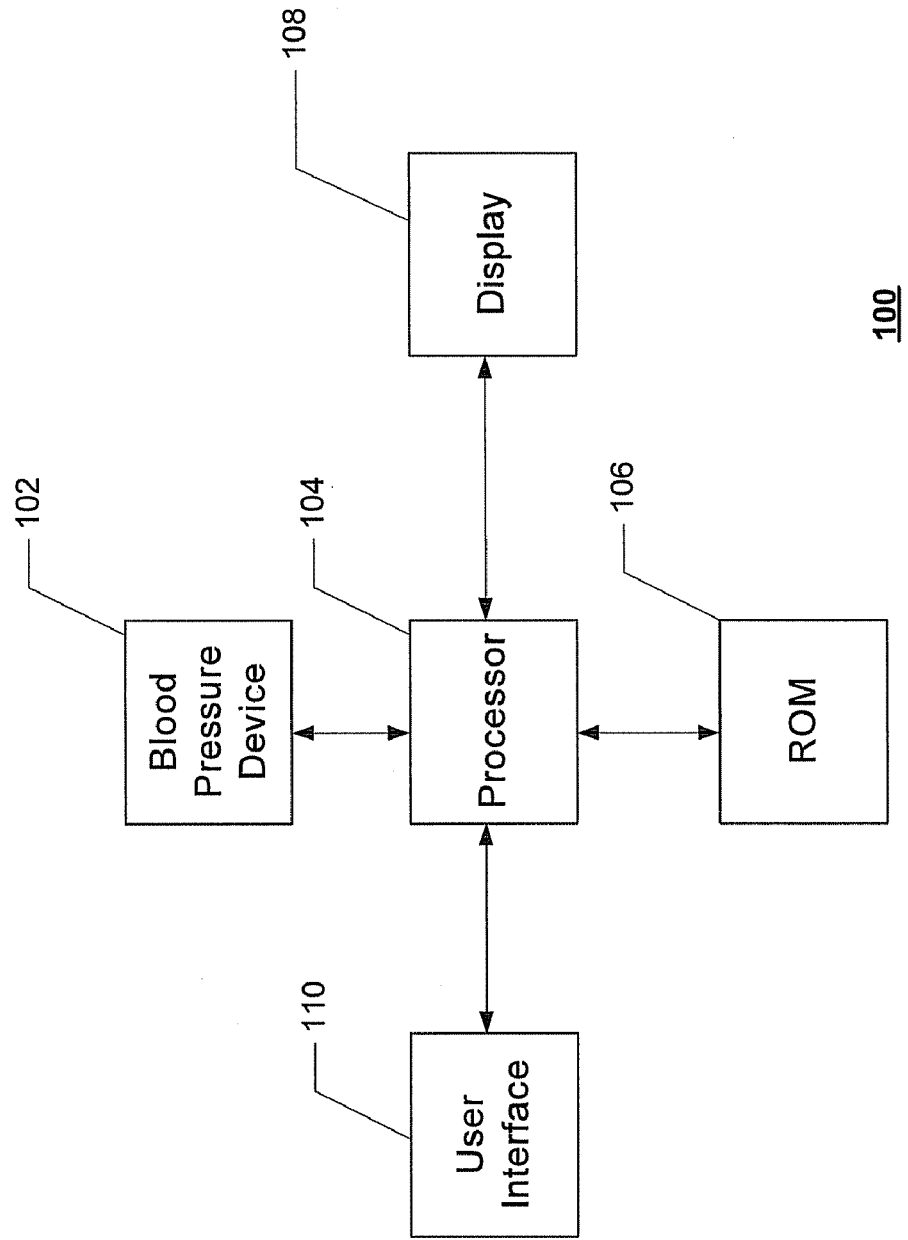

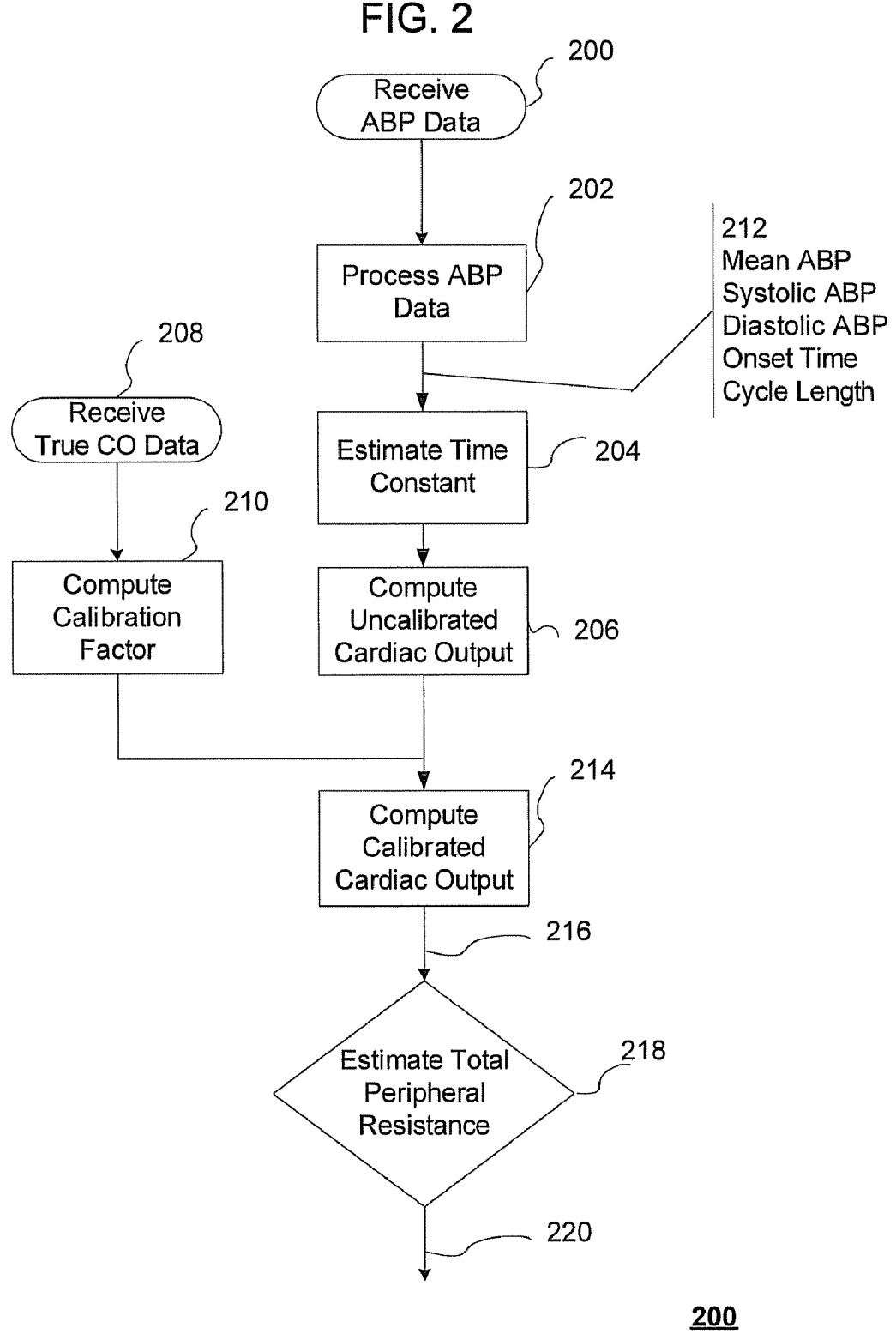

ABP waveform for circuit simulation with $P(0) = 0$ mmHg, $SV_n = 100$ ml, $R = 1$ mmHg/(ml/s), and $C = 2$ ml/mmHg.

FIG. 5

| Swine | CO (l/min) Range | HR (bpm) Range | Mean cABP (mmHg) Range | Duration of record (min) |
|---|---|---|---|---|
| 1 | 1.5-5.6 | 43-190 | 40-115 | 118 |
| 2 | 2.4-5.0 | 100-210 | 45-162 | 112 |
| 3 | 2.2-6.1 | 63-192 | 55-120 | 94 |
| 4 | 1.2-4.8 | 56-250 | 36-123 | 140 |
| 5 | 2.5-5.9 | 49-208 | 40-117 | 104 |
| 6 | 1.3-6.3 | 51-192 | 45-130 | 72 |

FIG. 6

| Animal | Number of comparisons | RMSNE (%) using cABP | RMSNE (%) using rABP | RMSNE (%) using fABP |
|---|---|---|---|---|
| 1 | 14604 | – | 15.4 | 10.2 |
| 2 | 14404 | 8.7 | 10.6 | 9.4 |
| 3 | 12088 | 8.8 | 9.7 | 8.8 |
| 4 | 18155 | 13.1 | 11.1 | – |
| 5 | 14113 | 10.6 | 8.4 | 12.6 |
| 6 | 9370 | 21.7 | 15.8 | 19.5 |
| Aggregate | 82734 | 11.6 | 11.9 | 12.1 |

FIG. 7

| – | ECO (for cABP) | ECO (for rABP) | ECO (for fABP) |
|---|---|---|---|
| TCO | 0.917±0.001 | 0.9325 ± 0.005 | 0.887 ± 0.002 |

FIG. 8

| –– | TCO-ECO (for cABP) | TCO-ECO (for rABP) | TCO-ECO (for fABP) |
|---|---|---|---|
| $V_a$ | 0.072±0.006 | 0.051 ± 0.007 | 0.009 ± 0.007 |
| HR | -0.470±0.005 | -0.488 ± 0.005 | -0.127 ± 0.006 |
| TCO | -0.102±0.006 | -0.198 ± 0.007 | 0.049 ± 0.007 |

FIG. 14

| Swine | Number of comparisons | RMSNE (%) using rABP | RMSNE (%) using fABP |
|---|---|---|---|
| 4 | 38 | 19.1 | 29.9 |
| 5 | 37 | 16.0 | 10.2 |
| 6 | 31 | 16.7 | 8.8 |
| 7 | 46 | 12.3 | — |
| 8 | 34 | 8.0 | 10.2 |
| 9 | 24 | 14.7 | 17.1 |
| Aggregate | 210 | 14.8 | 17.6 |

FIG. 15

| CO Estimation Method | $CO_n =$ | RMSNE (%) using rABP | RMSNE (%) using fABP |
|---|---|---|---|
| Our Method | (11) | 13.5 | 15.2 |
| Mukkamala [10] | ARMA model | 14.0 | 15.0 |
| Herd [9] | $C \cdot HR_n \cdot (\overline{P}_n - DAP_n)$ | 14.0 | 15.9 |
| Modified Mean Pressure | $C \cdot HR_n \cdot \overline{P}_n$ | 18.6 | 20.0 |
| Static Windkessel [12] | $C \cdot HR_n \cdot (SAP_n - DAP_n)$ | 21.1 | 18.8 |
| Liljestrand and Zander [6] | $C \cdot HR_n \cdot \left( \frac{SAP_n - DAP_n}{SAP_n + DAP_n} \right)$ | 30.0 | 25.1 |
| Mean Pressure | scaled $\overline{P}_n$ | 31.6 | 33.6 |

FIG. 16

| CO Estimation Method | Aggregate RMSNE (%) using rABP state-dependent calibration | Aggregate RMSNE (%) using rABP mean calibration |
|---|---|---|
| Ours | 11.8 | 13.5 |
| Herd [9] | 12.0 | 13.9 |
| Mukkamala et al. [10] | N/A | 14.0 |
| Liljestrand and Zander [6] | 14.6 | 30.0 |
| Modified Mean Pressure | 14.5 | 18.6 |
| Mean Pressure | 26.6 | 31.6 |

FIG. 18
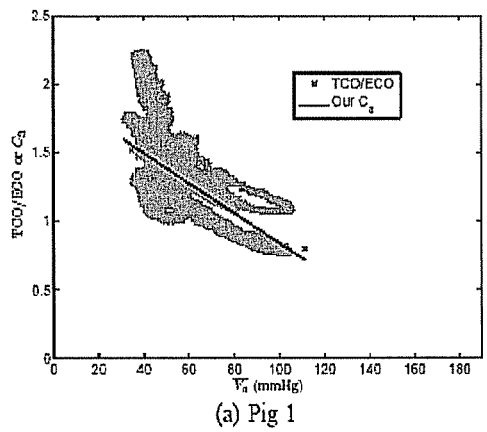
(a) Pig 1
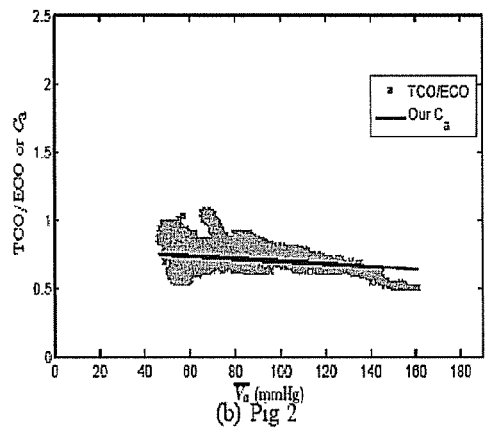
(b) Pig 2
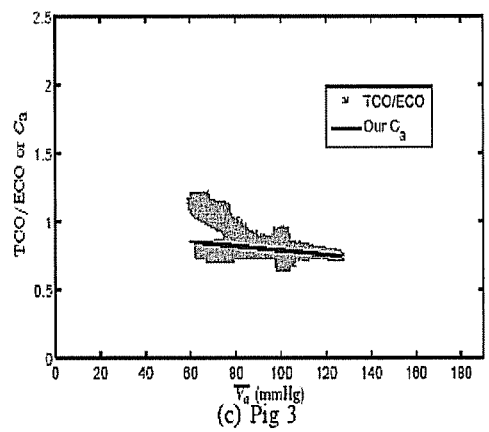
(c) Pig 3
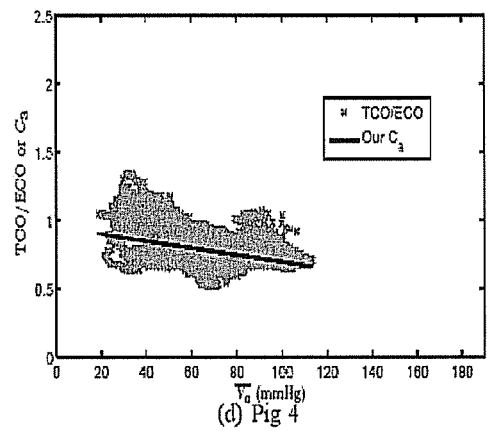
(d) Pig 4
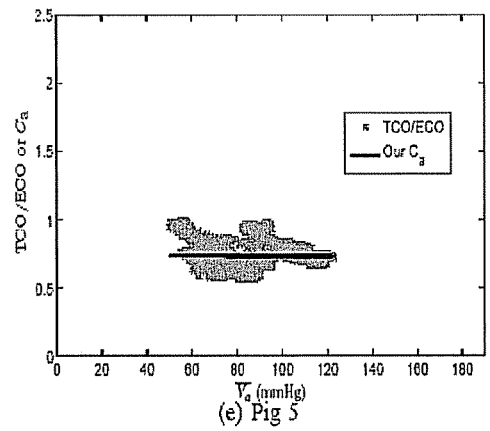
(e) Pig 5
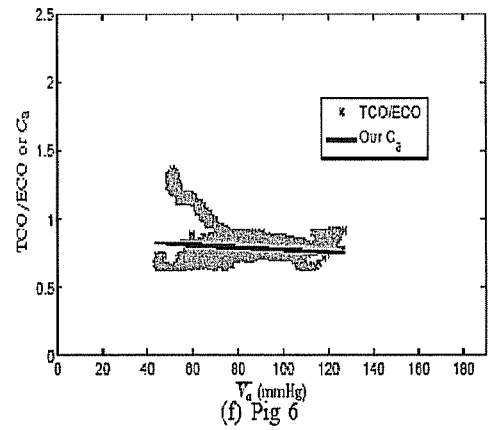
(f) Pig 6

FIG. 19

| Swine | Number of comparisons | RMSNE (%) for Herd estimate using rABP | RMSNE (%) for our estimate using rABP |
|---|---|---|---|
| 1 | 3256 | 17.1 | 14.9 |
| 2 | 2608 | 5.1 | 5.2 |
| 3 | 0 | — | — |
| 4 | 6847 | 14.8 | 14.2 |
| 5 | 0 | — | — |
| 6 | 514 | 9.3 | 7.1 |
| Aggregate | 13225 | 13.9 | 12.9 |

FIG. 20

| Swine | Number of comparisons | RMSNE (%) for Herd estimate using rABP | RMSNE (%) for our estimate using rABP |
|---|---|---|---|
| 1 | 3256 | 26.4 | 24.7 |
| 2 | 2608 | 5.5 | 6.0 |
| 3 | 0 | — | — |
| 4 | 6847 | 17.1 | 15.7 |
| 5 | 0 | — | — |
| 6 | 514 | 8.6 | 6.6 |
| Aggregate | 13225 | 18.2 | 16.9 |

SYSTEMS AND METHODS FOR MODEL-BASED ESTIMATION OF CARDIAC OUTPUT AND TOTAL PERIPHERAL RESISTANCE

CROSS REFERENCE TO RELATED APPLICATIONS

The instant application claims priority from provisional application No. 60/938,253 filed May 16, 2007, the disclosure of which is incorporated herein by reference in its entirety.

STATEMENT REGARDING FEDERALLY SPONSORED RESEARCH OR DEVELOPMENT

This invention was made with Government support under Contract No. R01 EB001659, awarded by the National Institutes of Biomedical Imaging and Bioengineering (NIBIB), a part of the National Institute of Health (NIH), and Grant No. CA00403, awarded by the National Space Biomedical Research Institute (NSBRI). The Government has certain rights in this invention.

FIELD OF THE INVENTION

This invention relates to cardiac output and total peripheral resistance estimation, and more particularly to cardiac output and total peripheral resistance estimation from peripheral or central arterial blood pressure waveforms.

BACKGROUND OF THE INVENTION

Cardiac output (CO) is the amount of blood the heart pumps out over a unit of time. Typical values of CO in resting adults range from 3 liters/minute to 6 liters/minute. One basis for estimating or measuring CO is the formula CO=HR×SV, where SV is cardiac stroke volume and HR is heart rate. If SV is measured in liters/beat and HR is measured in beats per minute, then CO is given in liters/minute, although any other units of volume and time may be used. Another basis for estimating or measuring CO is the formula CO=MAP/TPR, where MAP is mean arterial blood pressure and TPR is total peripheral resistance.

Cardiac output (CO) is a key hemodynamic variable that is commonly used to establish differential diagnoses, monitor disease progression, and titrate therapy in many cardiovascular conditions. For example, when combined with estimates of other hemodynamic variables such as mean arterial blood pressure (MAP) and total peripheral resistance (TPR), estimates of cardiac output may allow clinicians to determine the cause of circulatory shock [1]. (Numbers in square brackets refer to the reference list included herein. The contents of all these references are incorporated herein by reference.)

The current clinical gold-standard for measuring CO is intermittent thermodilution, a highly invasive procedure in which a balloon-tipped catheter (Swan-Ganz catheter [2]) is advanced to the pulmonary artery, a bolus of cold saline is injected into the circulation, and the blood's temperature profile is observed as a function of time. Due to its high degree of invasiveness, this procedure is usually reserved for only the sickest of patients, and even in critical care its benefit is increasingly questioned as retrospective clinical studies in the past ten years conclude that the use of a pulmonary artery catheter may not improve patient outcome [3], [4]. There are several patents that disclose systems directed to estimating CO via thermodilution. Some examples include U.S. Pat. No. 4,236,527 to Newbower et al., U.S. Pat. No. 4,507,974 to Yelderman, U.S. Pat. No. 5,146,414 to McKown et al., and U.S. Pat. No. 5,687,733 to McKown et al. The disadvantage of these systems is that they are highly invasive, and that CO can only be measured intermittently. In many situations, e.g. in critical care units, CO measurements via thermodilution may be made only every 2-3 days.

It is possible, however, to obtain estimates of cardiac output without using highly invasive procedures: rather than intermittently measuring average cardiac output invasively via thermodilution, many attempts have been made to estimate CO from the arterial blood pressure (ABP) waveform [5], [6], [7], [8], [9], [10], [11], using models of the arterial system. One of the most basic of these models is the Windkessel model [5] (see FIG. 3a), in which the arterial tree is modeled as a single, leaky pressurized chamber that is filled intermittently with boluses of fluid. Because HR is usually easy to measure using any of a wide variety of instruments, the calculation of CO usually depends on some technique for estimating stroke volume. Conversely, any method that yields a value for CO can be used to determine SV. In addition, estimates of CO (or SV) can be used with HR to estimate any parameter that can be derived from either of these values.

An entire class of patented or patent-pending algorithms is based on analyzing the pressure pulse morphology, often in the context of Windkessel-like models for the arterial tree [6], [7], [8], [9], [12]. Examples of these are U.S. Pat. No. 5,400, 793 to Wesseling, U.S. Patent Application Publication No. 20050124903 to Roteliuk et al., U.S. Patent Application Publication No. 20050124904 to Roteliuk, U.S. Patent Application Publication No. 20060235323 to Hatib et al., U.S. Patent Application Publication No. 20080015451 to Hatib et al., the contents of each of which are incorporated herein in their entirety. In many of these, since stroke volume is related to the arterial pressure pulse through the properties of the arterial tree, SV (and hence CO) is estimated on an intra-cycle timescale using morphological features of each individual ABP wavelet (such as systolic, mean, or diastolic ABP). One significant disadvantage of most of these methods or systems for estimating cardiac output is that they do not provide beat-to-beat estimates of cardiac output.

More recently, Cohen et al. ([10], [13], and U.S. Patent Application Publication No. 20040158163 to Cohen et al., the contents of which are incorporated herein in their entirety) intermittently, i.e. every 3 minutes, estimated relative changes in cardiac output from the inter-cycle (or beat-to-beat) variations of the ABP waveform, using these to determine the impulse response function of a model of significantly higher order than the Windkessel model and, from it, the time constant of arterial outflow that would be associated with a Windkessel model. Knowing the latter, the authors determined proportional CO, from which absolute CO can be obtained via calibration with a single or multiple reference CO measurements. In their calibration, Cohen et al. assume a linear relationship of arterial volume to mean pressure relationship, corresponding to constant lumped arterial tree compliance in the Windkessel model. Applicants' own interest in estimating CO and TPR derives from their own work in the area of cycle-averaged models of the cardiovascular system [14], [15], [16], where again the focus was on inter-cycle variation.

A criticism of Cohen et al. put forward in U.S. Patent Application Publication No. 20060235323 to Hatib et al. is that the approach disclosed by Cohen requires determination of a calibration factor on which accuracy of the CO measurement is closely dependent. Hatib et al. argue that Cohen's method ignores much of the information contained in the pressure waveform. In fact, as Hatib et al. note, one embodiment of Cohen's method uses only a single characteristic of each waveform, namely the area. Hatib et al. also note that a partial consequence of Cohen's greatly-simplified input signal to his recursive model is the need for a complicated transfer function model, which involves many zeroes, many poles, and, consequently, design and computational complexity.

However, Applicants note that the cardiac output estimation apparatus and methods described in U.S. Patent Application Publication No. 20050124903 to Roteliuk et al., U.S. Patent Application Publication No. 20050124904 to Roteliuk, U.S. Patent Application Publication No. 20060235323 to Hatib et al., U.S. Patent Application Publication No. 20080015451 to Hatib et al. (commonly owned by Edwards Life Sciences Corporation, hereinafter "Edwards") and in Cohen et al. explicitly assume an impulsive input flow waveform. Furthermore, the methods of Edwards and Cohen require a fixed sampling rate, i.e., the rate at which the impulsive input flow waveform is generated and/or sampled. There is a need for CO and TPR estimation methods that do not require the assumption of such an input waveform, and that do not require fixed sampling rates. The methods of Cohen and Edwards also explicitly use actual arterial blood pressure waveforms, which make them more susceptible to noise and artifacts inherent in these waveforms. There is a need for CO and TPR estimation methods that use parameters or variables derived from blood pressure waveforms instead of blood pressure waveforms that are sampled at a very high rate, e.g., 90 Hz or greater within each cycle.

The Edwards patents, collectively, and U.S. Pat. No. 5,400,793 to Wesseling (hereinafter "Wesseling") assume a 3-element Windkessel model in which a value for the input impedance of the model is either assumed or estimated. As the number of elements in a model increases, so does the complexity of the processing tasks that must be carried out to estimate CO or TPR. Therefore, the parameters and variables in this model cannot be easily estimated without making several assumptions, and requiring more input data than may be available in settings such as critical care units. The Edwards patents and Wesseling also describe calibration schemes for calibrating uncalibrated cardiac output, i.e., for calculating a multiplicative calibration factor that is used to obtain absolute cardiac output from proportional or relative cardiac output. In Edwards and Wesseling, the calibration scheme is dependent on coarse patient-specific data, e.g., height, body mass, age, gender. Wesseling's calibration factor has 3 parameters. In Edwards, the calibration factor furthermore requires the calculation of moments of the arterial blood pressure waveform. The calibration factors described in Edwards and Wesseling are complicated functions of three or more parameters which require several (at times, patient-specific) inputs. The Wesseling calibration factor is only grossly correlated to the cardiovascular system model he describes. There is still a need for simpler calibration factors that require fewer inputs and/or patient-specific parameters.

Although many CO estimation methods exist, as described above, there is still a need for CO estimation algorithms that are robust, and that effectively exploit both inter-cycle and intra-cycle variations in the blood pressure waveform. Thus, there is a need for CO and TPR estimation methods that use parameters or variables derived from blood pressure waveforms instead of highly-sampled blood pressure waveforms themselves. There also exists a need for CO estimation algorithms in which relative cardiac output estimates can be easily calibrated to obtain absolute cardiac output estimates. Thus, there is still a need for simpler calibration factors that require fewer inputs and/or patient-specific parameters. Current cardiac output estimation algorithms are not robust in the sense that they may perform well on a particular data set, but poorly on a different data set. There have been many methods in the past that seemed promising, but turned out not to work robustly. Furthermore, these CO estimation algorithms generally exploit either inter-cycle or intra-cycle variability. Currently, there are no algorithms for estimating cardiac output or total peripheral resistance that effectively exploit both inter-cycle and intra-cycle variations in the ABP waveform to estimate CO or TPR.

SUMMARY OF THE INVENTION

According to one aspect, the invention relates to a method for estimating beat-by-beat cardiovascular parameters and variables, comprising processing one or more cycles of arterial blood pressure to determine intra-beat and inter-beat variability in blood pressure, and computing estimates of one or more cardiovascular parameters and variables from the intra-beat variability, the inter-beat variability, and a beat-to-beat averaged Windkessel model of an arterial tree.

In an embodiment, the cardiovascular system parameters include a beat-by-beat time constant of the arterial tree. In an embodiment, the time constant is estimated over a data window. Optionally, the time constant is estimated through optimization of an error criterion. This error criterion may be a least-squared error criterion.

In certain embodiments, the cardiovascular system variables include an uncalibrated beat-by-beat cardiac output. In some embodiments, the method further comprises computing calibrated beat-by-beat cardiac output from the uncalibrated beat-by-beat cardiac output using a calibration factor. In an embodiment, the calibration factor is computed for each of the cycles.

In an embodiment, the calibration factor represents a lumped arterial compliance. This lumped arterial compliance may be modeled as a function of mean arterial blood pressure. Optionally, this lumped arterial compliance is modeled as a parameterized function of mean arterial blood pressure. Alternatively, this lumped arterial compliance is modeled as a two-parameter function of mean arterial blood pressure, or as a constant. The parameters of this lumped arterial compliance may be estimated through optimization of an error criterion. In some embodiments, the criterion is a least-squared error.

In another embodiment, the cardiovascular parameters include uncalibrated beat-by-beat total peripheral resistance. In some embodiments, the method further comprises computing calibrated beat-by-beat total peripheral resistance from the ratio of the time constant to a lumped arterial compliance. In an embodiment, the method further comprises computing calibrated beat-by-beat total peripheral resistance from the ratio of mean arterial blood pressure to calibrated cardiac output. In another embodiment, the method further comprises computing calibrated beat-by-beat total peripheral resistance from the ratio of mean pressure to a systemic blood flow. In some embodiments, the systemic blood flow is calibrated cardiac output minus the product of lumped arterial compliance with the ratio of beat-to-beat arterial blood pressure change to beat duration.

In some embodiments, the arterial blood pressure is measured at a central artery of the cardiovascular system. In other embodiments, the arterial blood pressure is measured at a peripheral artery of the cardiovascular system. In certain embodiments, the arterial blood pressure is measured using a noninvasive blood pressure device. This device may be a photoplethysmographic or tonometric blood pressure device.

In a further embodiment, processing the one or more cycles of arterial blood pressure includes obtaining values for mean blood pressure, diastolic blood pressure, and systolic blood pressure for each cycle. In some embodiments, processing the one or more cycles of arterial blood pressure includes obtaining an onset time for each cycle. In a further embodiment, processing the one or more cycles of arterial blood pressure includes computing a beat-to-beat arterial blood pressure change between consecutive onset times. Optionally, processing the one or more cycles of arterial blood pressure includes estimating pulse pressure in each cycle as a proportionality constant multiplied by a difference between mean pressure and diastolic pressure in each cycle. In some embodiments, the proportionality constant in each cycle is fixed. In some embodiments, the proportionality constant is greater than 1 and less than 4, but preferably 2. In certain embodiments, processing the one or more cycles of arterial blood pressure includes obtaining a beat duration for each cycle.

In another aspect, the invention relates to a system for estimating beat-to-beat cardiac output comprising a blood pressure measuring device, a processor, a display, a user interface, and a memory storing computer executable instructions, which when executed by the processor cause the processor to receive one or more cycles of arterial blood pressure from the blood pressure device, analyze one or more cycles of arterial blood pressure to determine intra-beat and inter-beat variability in blood pressure, compute estimates of one or more cardiovascular system parameters and variables from the intra-beat variability, the inter-beat variability, and a beat-to-beat averaged Windkessel model of an arterial tree, and display the estimates. In certain practice, the blood pressure device is a noninvasive blood pressure device. Optionally, this device may be a photoplethysmographic or a tonometric blood pressure device.

BRIEF DESCRIPTION OF THE DRAWINGS

The invention may be better understood from the following illustrative description with reference to the following drawings:

FIG. 1 is a block diagram of a system for estimating cardiac output and total peripheral resistance, according to an illustrative embodiment of the invention;

FIG. 2 is a process flow diagram suitable for estimating cardiac output and total peripheral resistance with the system of FIG. 1, according to an illustrative embodiment of the invention;

FIG. 3b is a graph illustrating a representative pulsatile arterial blood pressure waveform for the Windkessel circuit model of FIG. 3a;

FIG. 5 is a table showing the characteristics of a porcine data set according to an animal experiment disclosed herein;

FIG. 6 is a table summarizing the results of an animal experiment disclosed herein;

FIG. 7 is a table summarizing linear regressions of estimated versus true cardiac output for animal experiments disclosed herein;

FIG. 8 is a table summarizing linear regressions of estimated cardiac output versus heart rate, mean blood pressure, and true cardiac output for animal experiments disclosed herein;

FIG. 14 is a table summarizing the results of the application of the method of Cohen et al. described in U.S. Patent Publication 20040158163;

FIG. 15 is a table showing a comparison of Applicants' method for estimating cardiac output and other well-known methods from the literature;

FIG. 16 is a table showing a comparison of results using Applicants' mean pressure-dependent compliance calibration factor and a constant compliance calibration factor;

FIG. 18 includes graphs of the ratio of true to estimated cardiac output versus mean pressure for each of the animal experiments disclosed herein;

FIG. 19 is a table showing a comparison of results obtained using Applicants' method and the Herd method in which both sets of results are obtained using Applicants' mean pressure-dependent compliance calibration factor; and FIG. 20 is a table showing a comparison of results obtained using Applicants' method and the Herd method in which both sets of results are obtained using a constant compliance calibration factor.

DESCRIPTION OF CERTAIN ILLUSTRATIVE EMBODIMENTS

Figure 3A:
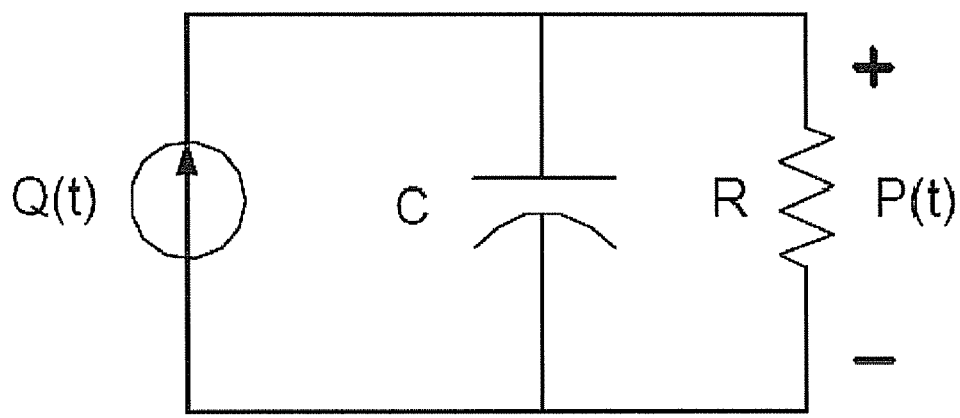
FIG. 3a is a circuit representation for the Windkessel model.

To provide an overall understanding of the invention, certain illustrative embodiments will now be described. However, it will be understood by one of ordinary skill in the art that the methods described herein may be adapted and modified as is appropriate for the application being addressed and that the systems and methods described herein may be employed in other suitable applications, and that such other additions and modifications will not depart from the scope hereof.

FIG. 1 is a block diagram of a cardiac output estimation system 100 in which the present invention's teachings may be implemented. The cardiac output estimation system 100 includes blood pressure measuring device 102, processor 104, memory 106 e.g. Read-Only Memory (ROM), display 108, and user interface 110. The processor 104 operates on blood pressure data in accordance with computer executable instructions loaded into memory 106. The instructions will ordinarily have been loaded into the memory from local persistent storage in the form of, say, a disc drive with which the memory communicates. The instructions may additionally or instead be received by way of user interface 110. The system may also receive user input from devices such as a keyboard, mouse, or touch-screen. Blood pressure measuring device 102 may be an invasive or a noninvasive device. Blood pressure measuring device 102 may be a photoplethysmographic or tonometric device. The blood pressure may be measured at a central, a pulmonary, or a peripheral artery in the cardiovascular system.

FIG. 2 is a process flow diagram 200 including steps 202, 204, 206, 208, 210, 216, and 218, suitable for estimating cardiac output and total peripheral resistance with the cardiac output estimation system 100 of FIG. 1, according to an illustrative embodiment of the invention. Blood pressure measuring device 102 measures arterial blood pressure waveforms and transmits the ABP waveform data to processor 104 of cardiac output estimation system 100 of FIG. 1. In step 202 of process 200, processor 104 of cardiac output estimation system 100 of FIG. 1 receives one or more cycles of ABP data and processes the ABP data. As will be explained in detail with reference to FIGS. 3 and 4, the outputs 212 of step 202 may include mean arterial blood pressure, diastolic arterial blood pressure, systolic arterial blood pressure, cycle onset time, and cycle length, for each of the received cycles of the arterial blood pressure. In step 204, as will be explained below in reference to FIGS. 3-20, processor 104 of cardiac output estimation system 100 estimates the time constant for a beat-to-beat averaged Windkessel model. This time constant is used in step 206, as explained below in reference to FIGS. 3-20, to obtain an uncalibrated estimate of cardiac output or total peripheral resistance. Calibrated cardiac output or total peripheral resistance may be obtained using true cardiac output measurements 208 and a model for a lumped arterial compliance calibration factor, as will be described below in reference to FIGS. 3-20, in steps 210 and 214. Total peripheral resistance may be estimated, as will be described below in reference to FIGS. 3-20. Some estimates of TPR may require the use of estimated calibrated cardiac output in step 218. The results of process 200 may include, among other cardiovascular system parameters and variables, estimated calibrated cardiac output 216 and estimated total peripheral resistance 220, as will be explained below in reference to FIGS. 3-20.

In this manner, cardiac output and total peripheral resistance may be estimated robustly because cardiac output estimation system 100 of FIG. 1 uses intra- and inter-beat variability in the arterial blood pressure waveforms, instead of the actual waveforms themselves. As will be described below in reference to FIGS. 3-20, the results obtained using the cardiac output estimation system 100 of FIG. 1 are much better than those obtained with other CO estimation systems or methods in the literature.

In the discussion below, Applicants will describe some embodiments in more detail. Applicants will begin with a description of the Windkessel model with reference to FIGS. 3a and 3b. Although only the two-element Windkessel model is presented here, the derivations and results can easily be extended to Windkessel models with 3 or more elements. This description will be followed by a derivation of the beat-to-beat averaged Windkessel model and a linear least-squares estimation of parameters and variables of this model, with reference to arterial blood pressure waveforms in FIG. 4. These waveforms are representative of those that may be processed at step 202 of FIG. 2 by cardiac output estimation system 100 of FIG. 1. Applicants conclude this section with a detailed description of experimental results using an animal (porcine or pig or swine) data set, with reference to FIGS. 5-20.

The Windkessel Model

The Windkessel model describes the basic morphology of an arterial pressure pulse [5]. It lumps the distributed resistive and capacitive properties of the entire arterial tree into two elements, as seen in the electrical circuit analog in FIG. 3a: a single resistor R, representing total peripheral resistance (TPR), and a single capacitor C, representing the aggregate elastic properties of all systemic arteries.

The differential equation representing the Windkessel circuit at time t is given by $$C\frac{dP(t)}{dt} + \frac{P(t)}{R} = Q(t) \tag{EQ. 1}$$

where P(t) represents arterial blood pressure at the aortic root at time t. In this application, at times Applicants use P and $V_u$ interchangeably. This equation shows that the time constant $\tau=RC$ governs the intra-cycle dynamics of the Windkessel model. The same time constant also governs the inter-cycle dynamics, as noted in [10], [14], [15].

The pumping action of the heart is represented by an impulsive current source Q(t) that deposits a stroke volume $SV_n$ into the arterial system during the $n^{th}$ cardiac cycle:

$$Q(t) = \sum_n SV_n \cdot \delta(t - t_n) \tag{EQ. 2}$$

where $t_n$ is the onset time of the $n^{th}$ beat and $\delta(t)$ is the unit Dirac impulse. It then follows by integrating (EQ. 1) over just the (infinitesimal) ejection phase that $$SV_n = C \cdot PP_n \tag{EQ. 3}$$

where $PP_n$ is the pulse pressure in the $n^{th}$ cardiac cycle, given by $PP_n=SAP_n-DAP_n$, with $SAP_n$ and $DAP_n$ being respectively systolic and diastolic arterial pressure in that cycle.

Figure 3B:
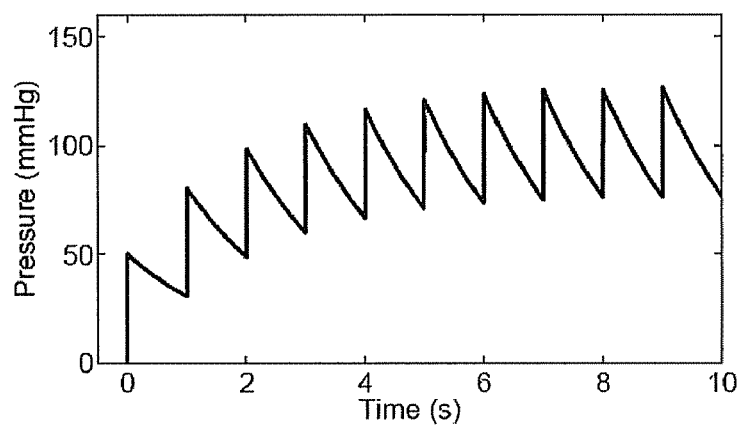

The pulsatile ABP waveform that results from simulating the model (EQ. 1) with P(0)=0 mmHg, $T_n$=1 s (such that heart rate in the $n^{th}$ cycle $HR_n$=60 bpm), $SV_n$=100 ml, R=1 mmHg/(ml/s), and C=2 ml/mmHg, is shown in FIG. 3b. The resulting steady-state pulse pressure equals 50 mmHg.

Applicants define $T_n$ to be the duration of the $n^{th}$ cardiac cycle, i.e., the beat that begins at time $t_n$ and ends at time $t_{n+1}$ (so $T_n=t_{n+1}-t_n$). It follows that the average cardiac output in the $n^{th}$ cycle is given by:

$$CO_n = \frac{SV_n}{T_n} = C_n\frac{PP_n}{T_n} \tag{EQ. 4}$$

where the first equality is simply the definition and the second follows on substituting from (EQ. 3).

Beat-to-Beat Averaged Windkessel Model

Given pulse pressure, (EQ. 4) may be used to estimate values of cardiac output. However, since the relation (EQ. 3) is based entirely on the essentially instantaneous ejection period assumed in this model, Applicants have recognized that the CO estimate obtained via (EQ. 4) does not take advantage of information from the remainder of the cardiac cycle that could be harnessed to provide a better-conditioned estimate. Specifically, the fact that (EQ. 1) interrelates the variables during the entire cardiac cycle, and indeed from one cycle to the next, has not been exploited in the derivation so far. Applicants recognize that to better reflect intra-cycle and inter-cycle behavior, one can average (EQ. 1) over an entire cardiac cycle rather than just the ejection phase as follows:

$$\frac{C_n}{T_n}\int_{t_n}^{t_{n+1}} \frac{dP(t)}{dt} dt + \frac{1}{T_n R_n}\int_{t_n}^{t_{n+1}} P(t)dt = \frac{1}{T_n}\int_{t_n}^{t_{n+1}} Q(t)dt. \quad \text{(EQ. 5)}$$

where the time constant $\tau_n = R_n C_n$, and where we consider $R_n$ and $C_n$ to be constant within each cardiac cycle, but allow them to vary from cycle to cycle. Note that in this application, the words cycle and beat are used interchangeably. This application of cycle-to-cycle or beat-to-beat averaging is an example of a general method known as the modulating function technique [17], first proposed by Shinbrot [18]. This averaging yields the following relation over the $n^{th}$ cycle [15]:

$$C_n \frac{\Delta P_n}{T_n} + \frac{\overline{P_n}}{R_n} = CO_n \quad \text{(EQ. 6)}$$

where $$\Delta P_n = P(t_{n+1}) - P(t_n) \quad \text{(EQ. 7)}$$

is the beat-to-beat pressure change at the onset times, and $$\overline{P_n} = \frac{1}{T_n}\int_{t_n}^{t_{n+1}} P(t)dt \quad \text{(EQ. 8)}$$

is the average or mean ABP computed over the $n^{th}$ cycle. Note that (EQ. 6) is a natural discrete-time counterpart to (EQ. 1), with the first and second terms now representing average flow through the capacitor and resistor, respectively, in the $n^{th}$ cycle.

Combining (EQ. 4) and (EQ. 6), one can obtain $$\frac{\Delta P}{T_n} + \frac{\overline{P_n}}{\tau_n} = \frac{PP_n}{T_n}, \quad \text{(EQ. 9)}$$

where $\tau_n = R_n C_n$ is the only unknown. Applicants refer to the model in (EQ. 9) as a beat-to-beat averaged Windkessel model. Note that this model has two elements and a source, and is thus a 2-element beat-to-beat averaged Windkessel model. Applicants note that this derivation, and its application in estimation cardiac output may be extended to Windkessel models with 3 or more elements.

Because determination of central $PP_n$ from peripheral pressure waveforms is problematic due to wave reflections, in one embodiment, Applicants use an expression presented in [9] to estimate $PP_n$ in terms of the mean pressure $\overline{P_n}$ in the $n^{th}$ cycle and $DAP_n$:

$$PP_n = \alpha(\overline{P_n} - DAP_n) \quad \text{(EQ. 10)}$$

where $\alpha$ is a constant. Assuming a triangular pulse shape yields $\alpha=2$ (see Appendix I), but Applicants' results on application of the CO estimation methodology are not extremely sensitive to the precise value of $\alpha$.

Figure 4:
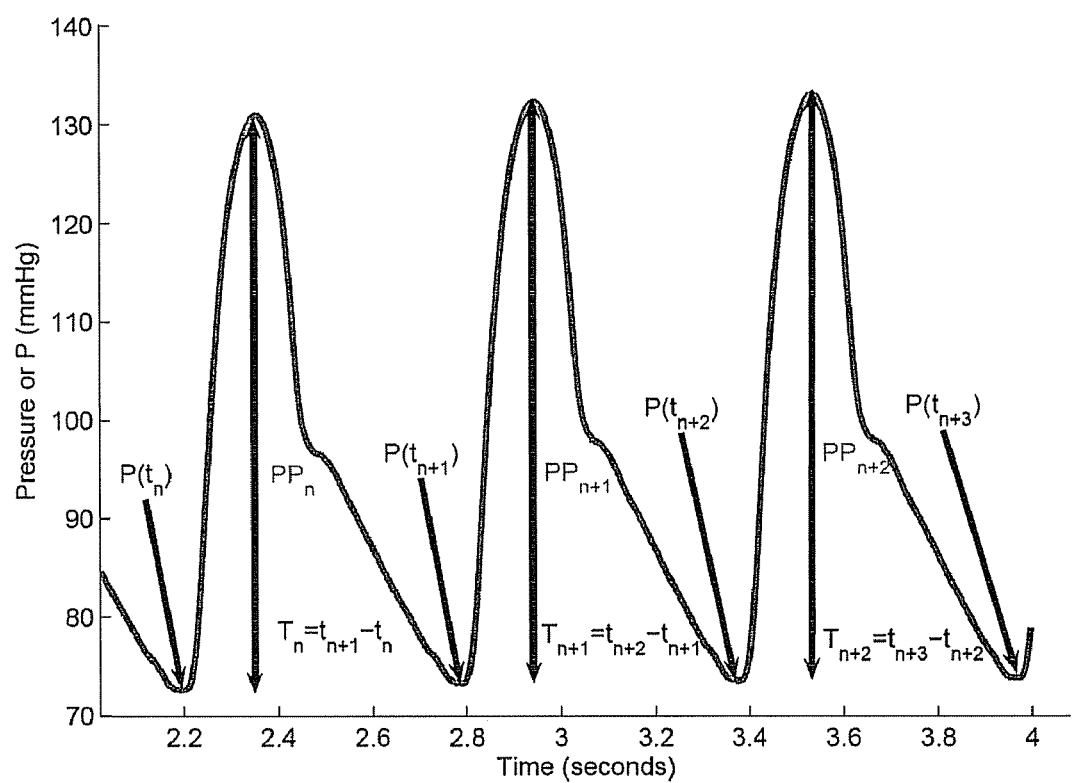
FIG. 4 is a graph of arterial blood pressure versus time showing a plurality of cycles of a porcine radial arterial blood pressure waveform.

(EQ. 9) may be used to estimate $1/\tau_n$ from knowledge of the remaining quantities, most of which are illustrated in FIG. 4. Applicants proceed to describe an estimation algorithm or scheme for estimating cardiac output based on the beat-to-beat averaged Windkessel model of (EQ. 9).

Estimation Using Least-Squares Error Criterion

Specifically, using a data window comprising an odd number of beats centered at n, and assuming $\tau_n$ to be essentially constant over this window, we invoke (EQ. 9) for each of the beats in the window to obtain a set of linear equations in the single unknown $1/\tau_n$, as illustrated in Appendix II. The least-square-error solution of this set yields the desired estimate. Repeating the process on a sliding window produces an estimate of $1/\tau_n$ for every beat. Cardiac output can now be estimated from (EQ. 6), rewritten below to show dependence on $1/\tau_n$:

$$CO_n = C_n\left(\frac{\Delta P_n}{T_n} + \frac{\overline{P_n}}{\tau_n}\right) \quad \text{(EQ. 11)}$$

Note that the term $$\left(\frac{\Delta P_n}{T_n} + \frac{\overline{P_n}}{\tau_n}\right)$$

is the uncalibrated beat-by-beat cardiac output. The conventional expression for calibrated or uncalibrated $CO_n$ neglects beat-to-beat variability and therefore omits the term $\Delta P_n/T_n$; it is thus actually valid only in cyclic steady state, while (EQ. 11) holds more generally. In cyclic steady-state, the first term on the right hand side of (EQ. 11) vanishes and the equation reduces to:

$$CO_n = \frac{\overline{P_n}}{R_n} \quad \text{(EQ. 12)}$$

which is simply the relation governing average flow through the resistor $R_n$ given the mean pressure $\overline{P_n}$. The vanishing term, $$\frac{\Delta P_n}{T_n}$$

in (EQ. 11), represents the average flow through $C_n$. It is a measure of the beat-to-beat or inter-beat or inter-cycle variability in cardiac output and allows us to fine tune our CO estimate. The term $$\frac{\overline{P_n}}{R_n}$$

is a measure of the intra-cycle or intra-beat variability. The determination of $C_n$ using calibration information is discussed in the next subsection.

Calibration of the Uncalibrated Beat-to-Beat Cardiac Output

To compute $CO_n$ using (EQ. 11), one may estimate the compliance $C_n$ by calibrating CO against one or more true or reference CO measurements. Note that in this application, true cardiac output is denoted TCO. A natural calibration criterion is the root-mean-square-normalized error (RMSNE) at the calibration points, as described in Appendix V, i.e., the points at which true or reference cardiac output measurements are available. If the compliance $C_n$ is assumed to be a constant equal to C, then it is straightforward to choose the C that minimizes the RMSNE [15]. Cohen et al. [10] instead used a mean calibration, dividing the mean of the true CO values by the mean of the estimated CO values at those points.

Considerably better results can be obtained by using a state-dependent model for $C_n$, namely to model the lumped arterial compliance as a function of arterial blood pressure. A simple choice is to assume an affine dependence of $C_n$ on mean arterial blood pressure, $\overline{P_n}$, as follows:

$$C_n = \gamma_1 + \gamma_2 \overline{P_n} \qquad \text{(EQ. 15)}$$

Though C may be expected to show a nonlinear dependence on mean arterial blood pressure, $\overline{P}$, we assume here that $\overline{P_n}$ changes slowly enough that $C_n$ may be assumed essentially constant over any window of a few beats or cycles in duration.

The calibration (EQ. 15) can be performed using a least-square-error solution to a linear system of equations as described in Appendix III. Other parameterizations may also be used, as discussed below and in Appendix III.

Estimation of Total Peripheral Resistance

Total peripheral resistance is also an important cardiovascular variable. In the clinical setting, TPR is defined as the ratio of mean arterial blood pressure to cardiac output. However, taking into account beat-to-beat variability as in (EQ. 11) and thereby accounting for transient flow into the arterial compliance, as was done by Toorop and co-workers [19], yields the modified expression for calibrated estimated beat-to-beat TPR:

$$R_n = \frac{\overline{P_n}}{CO_n - C_n \frac{\Delta P_n}{T_n}} \qquad \text{(EQ. 13)}$$

In another embodiment, Applicants estimate beat-to-beat TPR using:

$$R_n = \frac{\tau_n}{C_n} \qquad \text{(EQ. 14)}$$

Since both $\tau_n$ and $C_n$ may be outputs of our estimation method, (EQ. 14) may be easily implemented. In addition, if $C_n$ is not available, uncalibrated beat-to-beat TPR may be estimated as $R_n = \tau_n$, or by using the formula in (EQ 13) multiplied by $C_n$, and taking (EQ. 9) into account.

TPR estimate (EQ. 14) is relatively smooth given that $\tau_n$ and $C_n$ are estimated in a least-squares sense over a window of many beats. Since (EQ. 13) uses beat-to-beat variations in the flow to $C_n$, it tends to be noisier than (EQ. 14). Nonetheless, for all the results described later, Applicants used (EQ. 13) to estimate calibrated beat-to-beat TPR.

Animal Data Set and Experiments

Applicants have tested their CO estimation method as outlined above on the porcine dataset used by Cohen et al. [10]—a study on Yorkshire swine weighing 30-34 kg approved by the MIT Committee on Animal Care. The animals were intubated under anesthesia and mechanically ventilated. Once intubated, the animals' chests were opened, pressure and flow transducers were placed, and over the course of 2-3 hours, CO, ABP, and HR were varied by one or more of the following interventions: volume infusions, slow hemorrhage, intravenous (IV) drugs (one or more of phenylephrine, isoproterenol, esmolol, nitroglycerine, or dobutamine). FIG. 5 contains a table which gives a summary of population statistics for the six swine.

The data set contains measurements of ECG, central arterial blood pressure (cABP), radial arterial blood pressure (rABP), femoral arterial blood pressure (fABP), and aortic flow (AF), all sampled at 250 Hz with 16-bit amplitude resolution. The cABP waveform for swine 1 and the fABP waveform for swine 4 were corrupted because the pressure transducer measuring these variables were mis-calibrated during the experimental protocol. In addition, as was done in [10], data points at the end of each record, after progressive hemorrhage was started, were neglected as measured cardiac output was too low in these regions.

Using standard open-source algorithms [20], [21] on the AF waveform, Applicants derived onset times for each cardiac beat and HR. Applicants also calculated systolic and diastolic cABP, systolic and diastolic rABP, systolic and diastolic fABP, mean cABP, mean rABP, and mean fABP for each swine. True or reference beat-to-beat CO was calculated by averaging the AF waveform over each beat, and then applying a 50-beat median filter to the resulting output. All the data processing and cardiac output and TPR estimation algorithms were implemented in MATLAB™ R14 (Mathworks Inc., Natick, Mass.).

Experimental Results and Discussion

Unless noted otherwise, the results reported for estimated cardiac output, or ECO, herein were generated using a 100-point state-dependent, i.e., mean pressure-dependent calibration to obtain $C_n$ for each animal, as described in Appendix III. This amount of data represents less than 1% of each animal's data record, though the results change minimally if as few as 10 or as many as 1,000 points are used to calibrate. Also, all the results reported herein were obtained using the end-diastolic pressures in the expression for $\Delta P_n$. Applicants could also have used end-systolic pressures or pressures from another point in the arterial blood pressure waveform, too.

FIG. 6 contains a table summarizing the error obtained for each animal using either the cABP, rABP or fABP waveforms to estimate CO. Different window sizes and values of $\alpha$ in (EQ. 10) yield similar errors as shown in Appendix IV. Applicants' results show mean RMSNEs of about 12%, which is lower than the 15% reported in the literature as being acceptable for clinical purposes [13].

Figure 9:
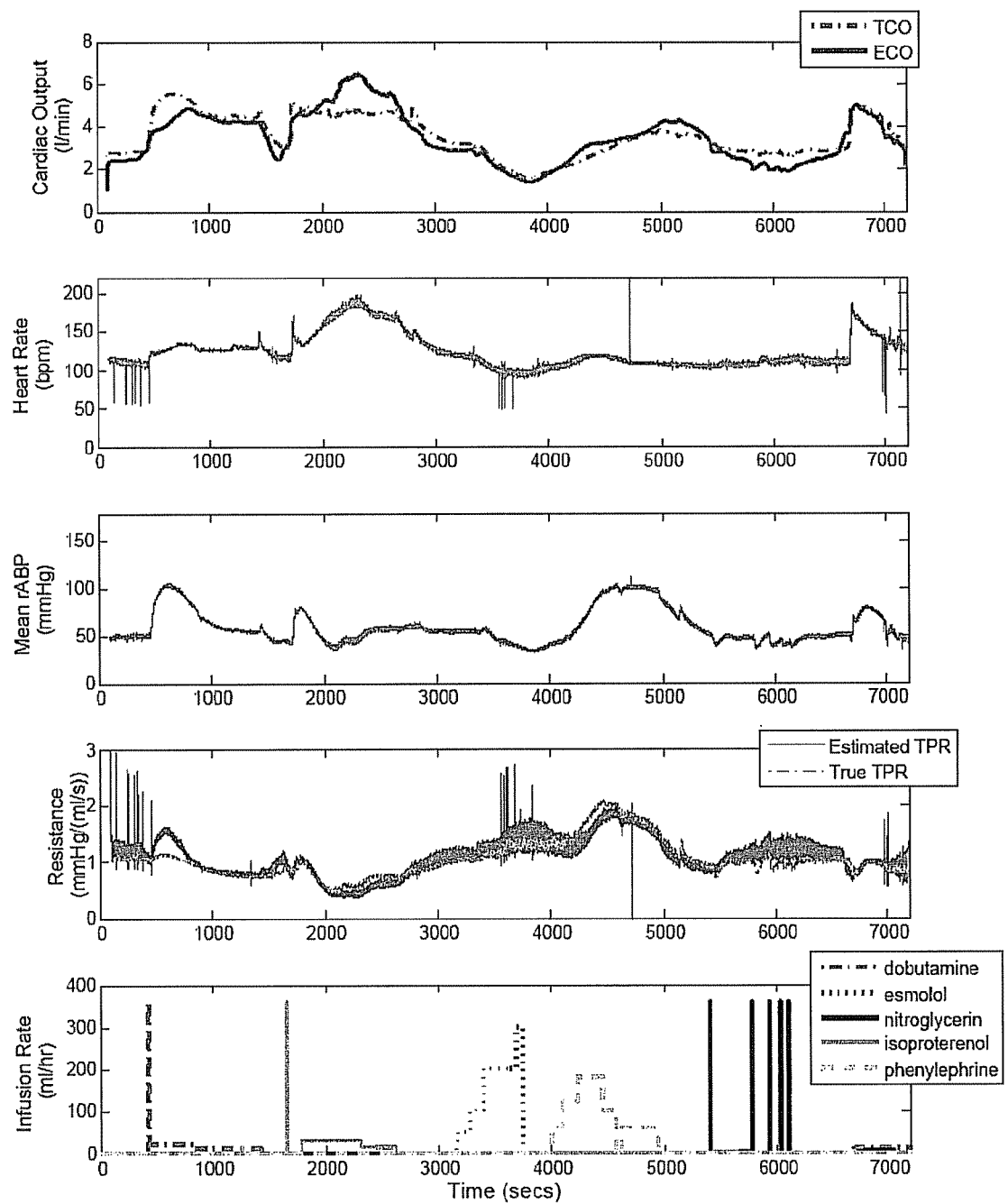
FIG. 9 includes graphs of true and estimated cardiac output and true and estimated total peripheral resistance according to a first animal experiment disclosed herein.
Figure 10:
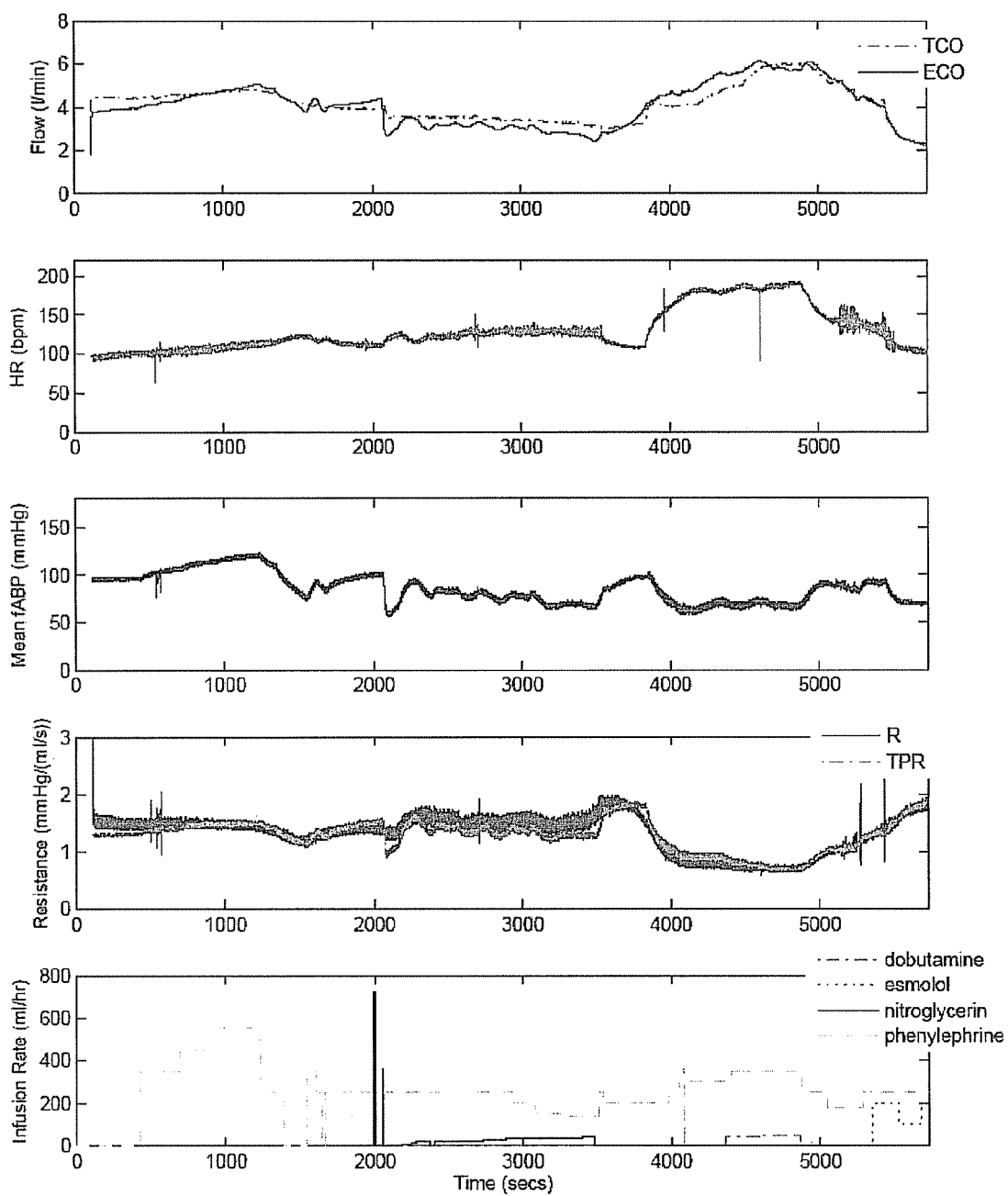
FIG. 10 includes graphs of true and estimated cardiac output and true and estimated total peripheral resistance according to a second animal experiment disclosed herein.
Figure 11:
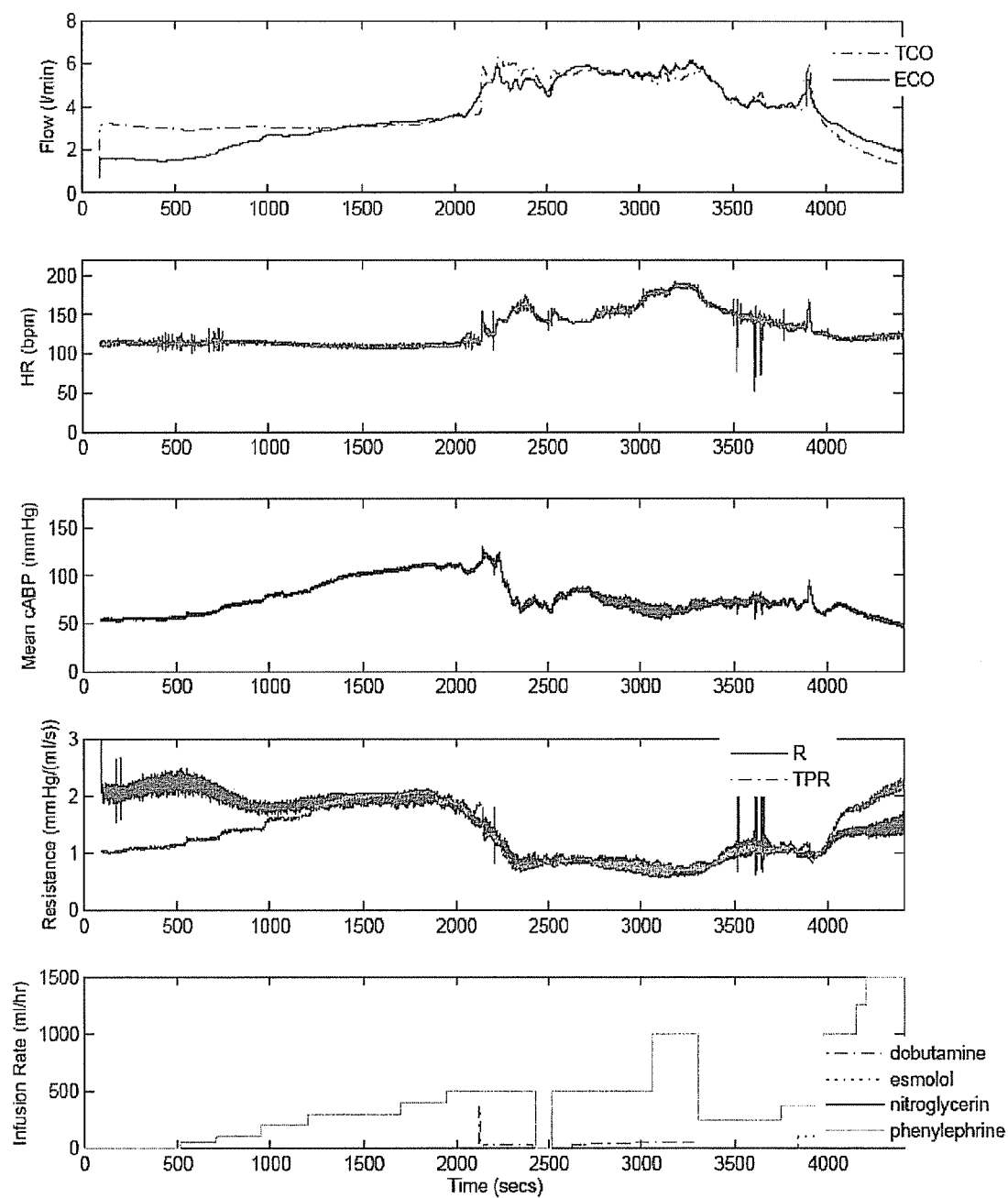
FIG. 11 includes graphs of true and estimated cardiac output and true and estimated total peripheral resistance according to a third animal experiment disclosed herein.

FIG. 9 shows the true and estimated CO, HR, mean rABP, true and estimated TPR, and drug infusions for Animal 1, FIG. 10 shows the true and estimated CO, HR, mean fABP, true and estimated TPR, and drug infusions for Animal 2, and FIG. 11 shows the true and estimated CO, HR, mean cABP, true and estimated TPR, and drug infusions for Animal 3. The spikes in the HR and R waveforms are a result of not filtering $T_n$ or $\Delta P_n$. In FIGS. 9, 10, and 11, Estimated CO and TPR track true CO and TPR very well while all major hemodynamic variables are varied independently over a wide range. Furthermore, due to the continuous nature of our CO and TPR estimates, we track the effects of pharmacological interventions quite closely.

Figure 12:
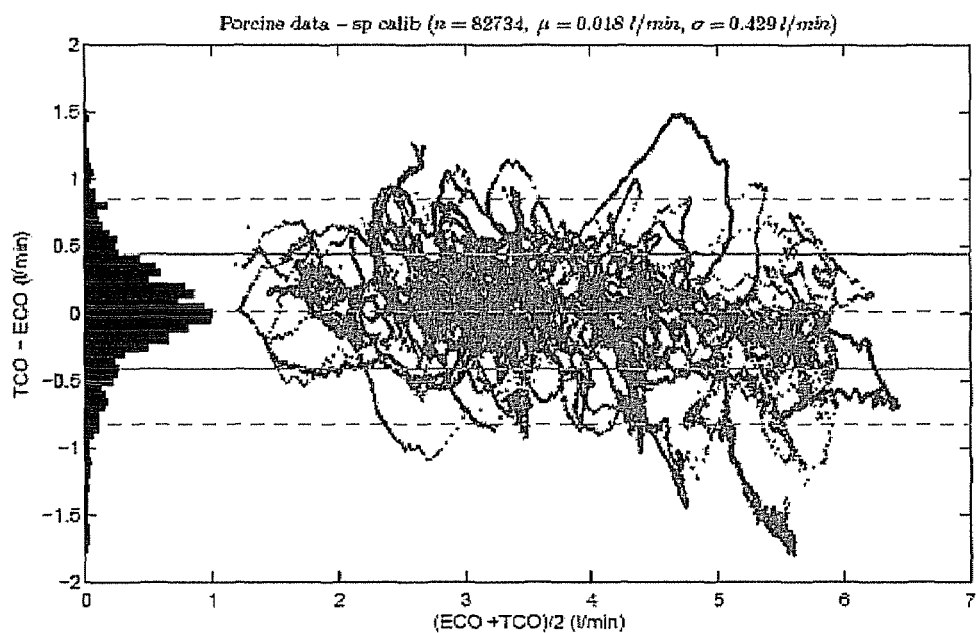
FIG. 12 is a Bland-Altman plot of cardiac output estimation error versus the mean of true and estimated cardiac output.

FIG. 12 is a Bland-Altman plot for the CO estimation error using rABP. This plot is an aggregate of all 82,734 comparisons listed in the table in FIG. 6. Note that 'sp calib' or 'sp calibration' denotes a 100-point state-dependent calibration, described in detail in Appendix III. The mean estimation error (or bias) is 18 ml/min, while the 1-standard deviation (SD) of the estimation error is 429 ml/min. The flow probe (T206 with A-series attachment, Transonic Systems Inc., Ithaca, N.Y.) used in the animal experiments had a relative precision of ±5%, which at the instrument scale of ±20 l/min is approximately 1 l/min. The 2-SD line for our estimate lies 860 ml/min from the line representing mean estimation error, showing that our method works very well when compared to the flow probe measurements.

Figure 13:
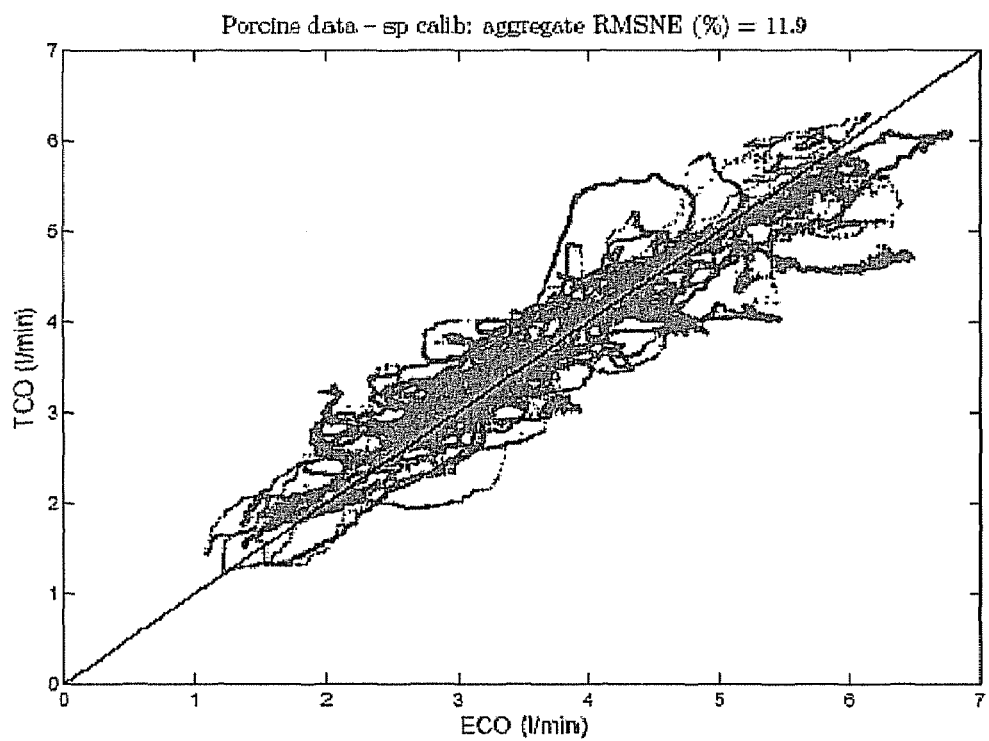
FIG. 13 is a graph of a linear regression of estimated versus true cardiac output.

FIG. 13 shows a linear regression visualizing the CO estimation error using rABP. This plot is an aggregate of all 82,734 comparisons listed in the table in FIG. 6. Note that sp calib or sp calibration denotes a 100-point state-dependent calibration, described in detail in Appendix III. The regression coefficients for ECO versus TCO (with 95% confidence intervals) are summarized in the table in FIG. 7. FIG. 8 contains a table which summarizes the correlation coefficients of the estimation error versus mean pressure, heart rate, and TCO, with 95% confidence levels. These correlation coefficients show that the estimation error is not strongly correlated with mean ABP, HR, or TCO.

Comparison of Experiment Results to other Windkessel-based CO Estimation Methods Applicants compared their animal experiment results to those obtained using the method of Cohen et al. and several Windkessel-based CO estimation methods. Mukkamala et al. [10] (Mukkamala and Cohen are co-inventors on the Cohen et al. patent referenced herein) reported the results shown in the table in FIG. 14, where Applicants calculated the aggregate RMSNEs using (EQ. 29). They re-sampled the 250 Hz data at 90 Hz, and used a 6-minute window size, with a 3-minute overlap between successive windows. In each 6-minute window, Mukkamala et al. estimated the time constant $\tau$ from the impulse response of the Windkessel model, which they estimated by assuming the Windkessel model could be represented by a 23-coefficient ARMA model with an impulsive pulse pressure source as its input [10]. In contrast, Applicants' model is a 2-element beat-to-beat averaged Windkessel model which does not assume a particular form of an impulsive input flow waveform.

Applicants' results are significantly different by swine and are, in an aggregate sense, much better than those reported in Mukkamala et al. [10]. In addition, instead of 6-minute windows, Applicants' method can use much less data e.g. 10-50 beats to obtain an estimate of $\tau_k$. A criticism of Mukkamala et al. put forward by van Lieshout et al. [22], and contended in [23], is that while CO estimates produced intermittently, e.g., every 3 minutes, may be good enough to track slower patient dynamics, they may not be good enough for large, sudden changes in CO, as is evident from patient data in the literature [24]. Furthermore, Cohen and co-workers' estimate assumes a constant arterial tree compliance, which is not necessarily a valid assumption, but does allow for the possibility of using only one true or reference CO point for calibration.

To do a fair comparison when comparing Applicants' estimated CO to the other Windkessel model-based estimates, Applicants used a mean calibration for each estimate. Applicants also calculated mean RMSNEs for each estimate method without weighting the individual swine RMSNEs by the number of comparisons in each swine record. The results of this analysis are shown in the table in FIG. 15. Overall, the results obtained by applying Applicants' method (even without the state-dependent calibration) and the methods proposed by Herd and Mukkamala produce essentially equivalent results, and they outperform the other methods tested. If Applicants were to apply the same 100-point state-dependent calibration on the Herd estimate, similar aggregate RMSNEs are obtained as in the table in FIG. 6. On the other hand, results obtained using human ICU data [25] show that the method of Liljestrand and Zander [6] outperforms the Windkessel model-based CO estimation methods we have used here [15]. In other published results on other human and animal data sets [15], Applicants' method performs much better than the Cohen et al., Herd, and Liljestrand and Zander methods [15].

Pressure-Dependent Lumped Arterial Compliance

In the human cardiovascular system, arterial tree compliance is a function of arterial blood pressure, and is perhaps better modeled as such rather than as a constant. Furthermore, it is well-known that arterial tree compliance depends on age (as we grow older, our arteries get less elastic and arterial compliance decreases [26], [27]), gender, and disease state, e.g., arteriosclerosis results in lower compliance [28]. However, this compliance also depends on arterial blood pressure.

Applicants investigated the use of both a constant and a state-dependent, i.e., mean pressure-dependent compliance in calibrating the uncalibrated beat-to-beat CO estimates. While there is much disagreement in the research community on this topic, CO estimation methods exist which assume a constant arterial compliance for calibration, while there are others which assume a pressure-dependent compliance function—whether linear or nonlinear.

Some previous work on CO estimation suggests that the arterial tree compliance is constant over a wide range of mean arterial blood pressures [8], [29], [30], [31]. However, there is no consensus on this observation. In fact, researchers have found that the calibration factor for cardiac output, the equivalent of arterial tree compliance, can vary significantly when estimating cardiac output (see FIG. 6 in [32], for example) in humans. While constant compliance may have been observed in the largest arteries in the body, it does not necessarily also hold true for the smaller arteries, as shown by Liu et al. [33] and Cundick et al. [32]. In addition, researchers such as Burattini et al. [34], who conducted canine experiments, have shown that arterial compliance can change drastically in response to vasoactive drugs—partly due to the effect of these drugs on the mean arterial blood pressure and partly due to drug-induced changes in the mechanical properties of the arterial wall.

Other researchers have carefully investigated total arterial compliance and its dependence on mean arterial blood pressure. Westerhof and co-workers [35], [19], [36], [37], for example, have argued that the arterial tree volume depends strongly on pressure—falling sharply at lower pressures and asymptotically converging to a maximum at high pressures. The (incremental) compliance, therefore, is large at low mean pressures and steadily decreases with increasing pressure. In their work, they explored the use of such a nonlinear arterial tree volume-pressure function in various incarnations of the Windkessel model. Liu et al. [33] compared several nonlinear arterial volume-pressure relationships, including logarithmic, piecewise-parabolic, and exponential relationships, and a specific linear volume-pressure relationship—with corresponding constant compliance. They argue that for the larger arteries, e.g., the aortic arch and thoracic aorta, a linear fit to the volume-pressure data was sufficient, but for the carotid, femoral, and brachial arteries, a nonlinear relationship fit the volume-pressure data better. In [38], [39], the authors proposed several nonlinear arterial volume-pressure functions and evaluated them using simulated and human data.

Of particular relevance in terms of CO estimation, is the arctangent volume-pressure curve proposed by Langewouters et al. [40] (note that Langewouters and Wesseling are co-workers) based on ex vivo studies of human thoracic and abdominal aortas. Their work was further strengthened by the work of Tardy et al. [41] who describe in vivo studies on the mechanical properties of human peripheral arteries. The relationship proposed by Langewouters and co-workers, and used by Wesseling et al. [7] in a CO estimation method, yields the following (incremental) arterial compliance, $C_a$:

$$C_a = \frac{\alpha_1}{\alpha_2 + \alpha_3(V_a - V^*)^2} \quad \text{(EQ. 16)}$$

where $\alpha_1$, $\alpha_2$, and $\alpha_3$ are constants, and $V^*$ is the inflection point of their arctangent aortic volume-pressure relationship. In humans, a value $V^*=40$ mmHg is suggested [7]. The constants $\alpha_1$, $\alpha_2$, and $\alpha_3$ depend on patient gender and age; nominal values of these constants can be extracted from regression analyses described in [40]. In contrast, Applicant's proposed calibration factor (EQ. 15) has only two parameters. Furthermore, it does not depend nonlinearly on pressure, making it much more amenable to a linear least-squares solution as described in Appendix III.

The CO estimation approach in [7] allows a further adjustment of $\alpha_1$ when calibrating against available CO measurements. There are other pressure-dependent compliances that have been used in CO estimation methods, e.g., the pressure-dependent compliances of Godje et al. [42] and Liljestrand and Zander [6]. In [6], compliance is simply modeled as being inversely proportional to the sum of the beat-to-beat systolic and diastolic arterial blood pressures, while in [42], compliance is modeled using a complicated expression that involves both mean and instantaneous arterial blood pressure.

In Applicants' own work, Applicants attempt to use either a linear arterial tree compliance as given by (EQ. 15) above, or a constant arterial tree compliance:

$$C_n = \gamma_1 \quad \text{(EQ. 17)}$$

which arises naturally from its linear counterpart (15) as the special case of $\gamma_2=0$.

The function (EQ. 15) corresponds to a parabolic volume-mean pressure relationship in the arterial tree, is simpler than the one used in [7], and facilitates estimation of patient- or animal-specific parameters from calibration data. A review of the literature shows no significant advantages of a logarithmic or arctangent volume-mean pressure relationship over one that is parabolic or one that uses instantaneous arterial blood pressure.

Figure 17:
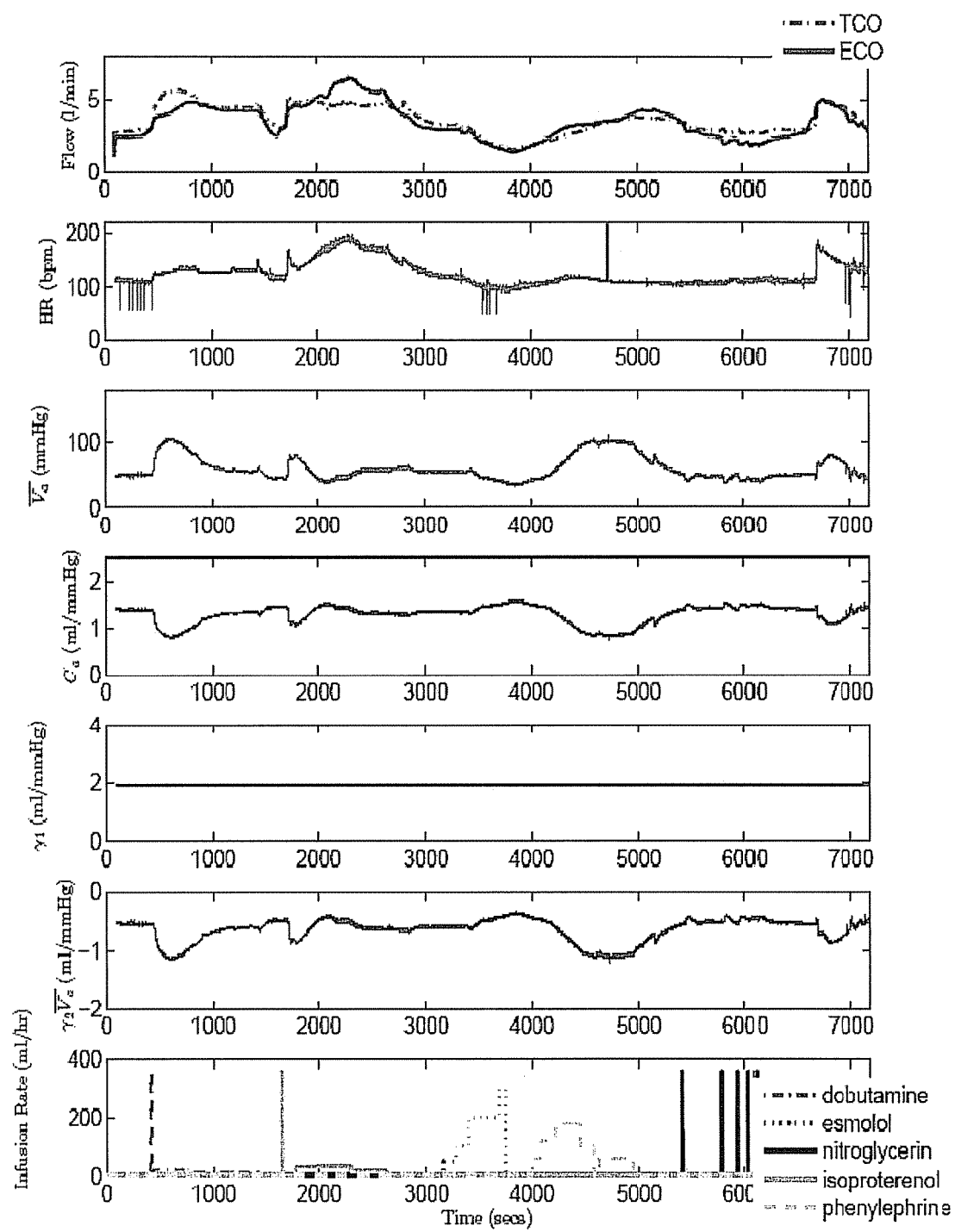
FIG. 17 includes graphs of true and estimated cardiac output and a mean pressure-dependent lumped arterial calibration factor according to a first animal experiment disclosed herein.

To test the hypothesis that a state-dependent compliance may be more appropriate than a constant compliance, Applicants applied an embodiment of their CO estimation method and other methods from the literature to the porcine data set using both a 100-point state-dependent calibration, and a 100-point mean calibration. These results may not be representative of other animal and/or human data sets as discussed in [15]. In each swine record, the points were spread evenly throughout each swine record. The results of this experiment are shown in the table in FIG. 16. It is clear that a state-dependent calibration, even on just 100 points out of 10,000-15,000 yields better results than a mean calibration. Applicants analyzed their linear mean pressure-dependent arterial tree compliance for each of the six swine and discovered that, apart from Swines 1, 4, and 6, all the swines have an almost-constant, i.e., pressure-independent, arterial compliance, except for certain sections of the data. FIGS. 17 and 18(a) show a time series of our fit for the arterial compliance, and a plot of true CO estimated CO and our fit for the arterial compliance versus mean pressure, respectively, for swine 1. Note that in FIG. 18, we used 100 points spread evenly throughout each swine record to compute our fit for the arterial compliance C. Graphs of true CO/estimated CO and our fits for the arterial compliance versus mean pressure for all six swine appear in FIG. 18.

It is clear from FIGS. 17 and 18, that for the majority of the data points in each swine record, the arterial tree compliance is essentially constant. Thus, for all but two of the swines in this data set—swines 1 and 4—we can assume that $\gamma_2$ in (EQ. 15) is zero, except for certain sections of the data. Thus, for all but swine 4, there are sets of data points, particularly at lower mean pressures, which would be well captured by a linear compliance instead of a constant compliance.

Inter-Beat or Beat-to-Beat Variability

The table in FIG. 16 seems to imply that the Herd CO estimation method and Applicants CO estimation method are, in an aggregate sense, equivalent. However, the same is not true if Applicants take a closer look at the true and estimated CO waveforms, particularly in sections where inter-beat variability is high.

Applicants CO estimation method incorporates, among other things, beat-to-beat variability and therefore may produce more accurate CO estimates than those produced by many intra-beat CO estimation methods. To test this hypothesis, i.e., that beat-to-beat variability improves our CO estimate, Applicants define a beat-to-beat variability index, $B2BVI_b$ (%), in each 360-beat window as follows:

$$B2BVI_b = \frac{1}{360} \sum_{n=b}^{b+360} \left(100 \frac{\Delta P_n}{PP_n}\right). \quad \text{(EQ. 18)}$$

Applicants calculated RMSNEs only using points on the estimated CO waveform where $\tau_n$ was calculated on windows where $B2BVI_b \geq 5\%$. The results obtained are summarized in the tables of FIGS. 19 and 20, where Applicants' estimate is compared to the results obtained using the Herd estimation method. For some animals, there were no such windows as depicted with a '-' in the table. It is clear that on windows with high beat-to-beat variability, Applicants' CO estimates performs either comparably (in the case of swine 2) or a lot better than the Herd estimate. This result is independent of whether a mean or a state-dependent calibration is performed, as seen in FIGS. 19 and 20. Thus, in data segments in which beat-to-beat variability is significant, as reflected by the ratio $\Delta P_n PP_n$ in (EQ. 18), Applicants' method does substantially better than static pulse contour methods, such as the Herd method, that solely analyze the intra-beat pulse shape.

Appendix I: Derivation for a in (EQ. 10)

In an embodiment, if one assumes a high enough HR (i.e. $T_n \ll \tau_n$) in the $n^{th}$ cardiac cycle of the Windkessel model (EQ. 1), one can see that in the $(n+1)^{st}$ cardiac cycle, diastolic ABP is given by $$DAP_{n+1} = SAP_n e^{-\frac{T_n}{\tau_n}} \approx SAP_n \left[1 - \frac{T_n}{\tau_n}\right] \quad \text{(EQ. 19)}$$

such that the mean ABP in the $n^{th}$ cardiac cycle may be approximated as $$\overline{P_n} \approx \frac{1}{T_n}\left[DAP_{n+1}T_n + \frac{1}{2}T_n(SAP_n - DAP_n)\right] \quad \text{(EQ. 20)}$$

which yields the following formula for pulse pressure in the $n^{th}$ cardiac cycle:

$$PP_n = SAP_n - DAP_n \approx 2(\overline{P_n} - DAP_n). \quad \text{(EQ. 21)}$$

Appendix II: More on Linear Least-Squares Estimation for $1/\tau_n$

In an embodiment described above, Applicants assumed that $1/\tau_n$ varies slowly from beat-to-beat and that it stays fixed over several beats. Had Applicants not assumed an impulsive cardiac ejection in (EQ. 3), there would have been two unknowns in (EQ. 9), and Applicants would have had to make the assumption that both $1/\tau_n$ and $$\frac{SV_n}{C_n}$$

vary slowly from beat-to-beat. Such an assumption may be invalid for stroke volume as it can change rapidly from one beat to the next. In addition, depending on the data set used, the resulting two-parameter least-squares estimation problem may be ill-conditioned. However, in some embodiments, the resulting two-parameter least-squares estimation problem may be feasible and well-conditioned.

Applicants estimated CO directly from (EQ. 9) by computing a least-squares estimate of $1/\tau_n$ over a data window, i.e., Applicants calculated a least-squares estimate of $1/\tau_n$ for the $n^{th}$ beat using a window comprising the k/2 adjacent beats on each side of this beat. This results in a total of k (even) equations in one unknown, a well-conditioned least-squares estimation problem as shown immediately below:

$$\begin{bmatrix} -\overline{P}_{n-\frac{k}{2}} \\ \vdots \\ -\overline{P}_{n+\frac{k}{2}} \end{bmatrix} \begin{bmatrix} \frac{1}{\tau_n} \end{bmatrix} = \begin{bmatrix} \frac{\Delta P_{n-\frac{k}{2}}}{T_{n-\frac{k}{2}}} - \frac{PP_{n-\frac{k}{2}}}{T_{n-\frac{k}{2}}} \\ \vdots \\ \frac{\Delta P_{n+\frac{k}{2}}}{T_{n+\frac{k}{2}}} - \frac{PP_{n+\frac{k}{2}}}{T_{n+\frac{k}{2}}} \end{bmatrix} \quad \text{(EQ. 22)}$$

In one embodiment, Applicants assign the estimate $1/\tau_n$ from each window to the midpoint of that window, and set n>k/2 in (EQ 22).

Appendix III: More on Calibration Methods

In calibrating the uncalibrated beat-to-beat cardiac output estimates, one may attempt to find a value for $C_n$ such that the CO estimation error, $\epsilon_n$, in $$CO_n = C_n UCO_n + \epsilon_n \quad \text{(EQ.23)}$$

is minimized, in some sense, for all n of interest. Note that in (EQ. 23), we define uncalibrated cardiac output, or UCO, by:

$$UCO_n = \left( \frac{\Delta P_n}{T_n} + \frac{\overline{P}_n}{\tau_n} \right) \quad \text{(EQ. 24)}$$

For example, one can find $C_n$ such that the root-mean-square-normalized-error (RMSNE), described in the Appendix V, is minimized, i.e., find the optimal $C_n$ such that $$\frac{\epsilon_n}{CO_n}$$

in $$1 = \frac{C_n UCO_n}{CO_n} + \frac{\epsilon_n}{CO_n} \quad \text{(EQ. 25)}$$

is minimized, in the least-squares sense, for all k of interest. Note that this kind of least-squares calibration may be done because of the simple form for $C_n$ in (EQ. 15).

In another embodiment, one may proceed as follows: given a set of CO measurements at points $\{p_1, \ldots, p_n,\}$, $\{CO_{pi}\}$, find the least-squares optimal $\gamma_1$ and $\gamma_2$ in (EQ. 15), by solving (EQ. 25) using at least two reference or true CO (TCO) measurements:

$$\begin{bmatrix} \frac{UCO_{p_1}}{CO_{p_1}} & \overline{P}_{p_1} \frac{UCO_{p_1}}{CO_{p_1}} \\ \vdots & \vdots \\ \frac{UCO_{p_n}}{CO_{p_n}} & \overline{P}_{p_n} \frac{UCO_{p_n}}{CO_{p_n}} \end{bmatrix} \begin{bmatrix} \gamma_1 \\ \gamma_2 \end{bmatrix} = \begin{bmatrix} 1 \\ \vdots \\ 1 \end{bmatrix} \quad \text{(EQ. 26)}$$

for $n \geq 2$. For (EQ. 26) to be well-conditioned, there should be enough variation in mean pressure $\overline{P}_k$. If we solve (EQ. 26) using at least two equally-spaced true CO measurements, Applicants call this a two-point state-dependent calibration. In the results described in this application, a 100-point state-dependent calibration was used. A state-dependent calibration may be more realistic in settings such as the intensive care unit (ICU) where CO is measured only intermittently.

The results reported in Mukkamala et al. [10] were generated using a $C_n$ that is not optimal in the sense of (EQ. 25). In Mukkamala et al. [10], a mean calibration was done such that:

$$C_n = C = \frac{\text{mean}(C)}{\text{mean}(UCO)}. \quad \text{(EQ. 27)}$$

This calibration is equivalent to assuming that $\gamma_2$ in (EQ. 15) equals 0 and that $\gamma_1$ is given by (EQ. 27) above.

Appendix IV: Results for Different Data Window Sizes and Values of $\alpha$

Applicants used various window sizes (i.e. number of beats)—roughly ranging from 6 seconds to 12 minutes of data—to estimate $\tau_n$, and hence $CO_n$. Applicants observed that mean RMSNEs do not change significantly for window sizes above 50 beats, implying that one does not seem to need variability beyond the range of a 50 beats (or 30 seconds at a resting porcine heart rate of 100 bpm) to obtain reasonable calibrated beat-to-beat CO estimates. This observation, however, could be strongly dependent on the porcine data set used.

In various embodiments, Applicants have used various values for $\alpha$ in (EQ. 10) to estimate $CO_n$. With a window size equal to 360 beats, the mean RMSNE taken over the six swine for each value of a were about the same for a ranging from 1.5 to 100. For small $\alpha$ e.g. $\alpha \approx 0.01$-0.9, the mean RMSNEs are much higher than with $\alpha \geq 1.5$. For other window sizes, the same result holds i.e. the mean RMSNEs are not too sensitive to the value of $\alpha$ except for small $\alpha$. From a least-squares estimation point of view, this is not surprising as the constant $\alpha$ must be large enough that the term $$\frac{1}{T_n} PP_n$$

in (EQ. 9) is of the same order of magnitude as, i.e. significant, as the term $$-\frac{\overline{P}_n}{\tau_n}.$$

Appendix V: Root Mean Square Normalized Error

In comparing true cardiac output to estimated cardiac output (ECO), Applicants used a root-mean-square-normalized-error criterion. For a particular swine, e.g. swine i, given $n_i$ points at which true CO was measured and CO was estimated, the RMSNE (in %) for the CO estimate for swine i, denoted $RMSNE_{swine_i}$, is given by the following formula:

$$RMSNE_{swine_i} = \sqrt{\frac{1}{n_i}\sum_{n=1}^{n_i}\left(\frac{100(trueCO_n - estimatedCO_n)}{trueCO_n}\right)^2}. \quad (EQ.\ 28)$$

As the swine data records were of varying lengths, the "aggregate" RMSNE over all the swines was calculated as the weighted average of the individual swine RMSNEs. Assuming that $\Sigma_i n_i = N$, the RMSNE over all swines is given by:

$$RMSNE = \sqrt{\frac{1}{N}\sum_i n_i (RMSNE_{swine_i}^2)}. \quad (EQ.\ 29)$$

Note that RMSNE is an aggregate measure of performance. While it represents how the true CO and estimated CO compare in an average sense, it does not classify the CO estimation error with regard to the particular values of CO, ABP, or HR, or even the particular interventions being performed on the animals. A linear regression of true CO versus estimated CO with a reported correlation coefficient may also only be an aggregate measure of performance, as would a Bland-Altman (see [43], [44]) plot of CO error versus the mean of true CO and estimated CO.

The invention may be embodied in other specific forms without departing from the spirit or essential characteristics thereof. The forgoing embodiments are therefore to be considered in all respects illustrative, rather than limiting of the invention.

Reference Listing

[1] M. Hadian and M. R. Pinsky, "Functional hemodynamic monitoring," Current opinion in critical care, vol. 13, pp. 318-323, 2007.

[2] H. Swan, W. Ganz, and J. F. et al., "Catheterization of the heart in man with the use of a flow-directed balloon-tipped catheter," N Engl. J. Med., vol. 283, pp. 447-451, 1970.

[3] S. Harvey and M. Singer, "Managing critically ill patients with a pulmonary artery catheter," British journal of hospital medicine, vol. 67, no. 8, pp. 421-426, 2006.

[4] G. Rubenfeld, E. McNamara-Aslin, and L. Rubinson, "The pulmonary artery catheter, 1967-2007: Rest in peace?," JAMA, vol. 298, no. 4, pp. 458-461, 2007.

[5] O. Frank, "Die Theorie der Pulswelle," Z. Biol., vol. 85, pp. 91-130, 1927.

[6] G. Liljestrand and E. Zander, "Vergleichende Bestimmung des Minutenvolumens des Herzens beim Menschen mittels der Stickoxydulmethode und durch Blutdruckmessung," Z. Exp. Med., vol. 59, pp. 105-122, 1928.

[7] K. Wesseling, J. Jansen, J. Settels, and J. Schreuder, "Computation of aortic flow from pressure in humans using a nonlinear, three-element model," J. Appl. Physiol., vol. 74, no. 5, pp. 2566-2573, 1993.

[8] M. Bourgeois, B. Gilbert, D. Donald, and E. Wood, "Characteristics of aortic diastolic pressure decay with application to continuous monitoring of changes in peripheral vascular resistance," Circ. Res., vol. 35, no. 1, pp. 56-66, 1974.

[9] J. Herd, N. Leclair, and W. Simon, "Arterial pressure pulse contours during hemorrhage in anesthetized dogs," J. Appl. Physiol., vol. 21, no. 6, pp. 1864-1868, 1966.

[10] R. Mukkamala, A. Reisner, H. Hojman, R. Mark, and R. Cohen, "Continuous cardiac output monitoring by peripheral blood pressure waveform analysis," IEEE Trans. Biomed. Eng., vol. 53, no. 3, pp. 459-467, 2006.

[11] C. K. Hofer, M. T. Ganter, and A. Zollinger, "What technique should I use to measure cardiac output?," Current opinion in critical care, vol. 13, pp. 308-317, 2007.

[12] O. Frank, "Schätzung des Schlagvolumens des menschlichen Herzens auf Grund der Wellen-und Windkessel-theorie," Z. Biol., vol. 90, pp. 405-409, 1930.

[13] Z. Lu and R. Mukkamala, "Continuous cardiac output monitoring in humans by invasive and noninvasive peripheral blood pressure waveform analysis," J. Appl. Physiol., vol. 101, no. 2, pp. 598-608, 2006.

[14] T. Parlikar, T. Heldt, and G. Verghese, "Cycle-averaged models of cardiovascular dynamics," IEEE Trans. on Circ. Syst.: I, vol. 53, no. 11, pp. 2459-2468, 2006.

[15] T. Parlikar, Modeling and Monitoring of Cardiovascular Dynamics for Patients in Critical Care. Ph.D. Thesis, Massachusetts Institute of Technology, Cambridge, Mass., June 2007.

[16] T. A. Parlikar, T. Heldt, G. V. Ranade, and G. C. Verghese, "Model-based estimation of cardiac output and total peripheral resistance," Computers in Cardiology, vol. 34, pp. 379-382, 2007.

[17] H. Unbehauen and G. Rao, Identification of continuous systems, vol. 10 of Systems and Control Series. North-Holland, 1987.

[18] M. Shinbrot, "On the analysis of linear and nonlinear systems," Transactions of the ASME, vol. 79, pp. 547-552, 1957.

[19] G. Toorop, N. Westerhof, and G. Elzinga, "Beat-to-beat estimation of peripheral resistance and arterial compliance during pressure transients," J. Appl. Physiol. Heart Circ. Physiol., pp. H1275-H1283, 1987.

[20] W. Zong, T. Heldt, G. Moody, and R. Mark, "An open-source algorithm to detect onset of arterial blood pressure pulses," Computers in Cardiology, vol. 30, pp. 259-262, 2003.

[21] W. Zong, G. Moody, and D. Jiang, "A robust open-source algorithm to detect onset and duration of QRS complexes," Computers in Cardiology, vol. 30, pp. 737-740, 2003.

[22] J. van Lieshout and J. Jansen, "Continuous cardiac output monitoring by blood pressure analysis," J. Appl. Physiol., vol. 102, p. 826, February 2007.

[23] R. Mukkamala and A. Reisner, "Reply to van Lieshout and Jansen," J. Appl. Physiol., vol. 102, p. 827, February 2007.

[24] T. Heldt, "Continuous blood pressure-derived cardiac output monitoring—should we be thinking long-term?," J. Appl. Physiol., vol. 101, no. 2, pp. 373-374, 2006.

[25] J. X. Sun, A. T. Reisner, M. Saeed, and R. G. Mark, "Estimating cardiac output from arterial blood pressure waveforms: a critical evaluation using the MIMIC-II database," Computers in Cardiology, vol. 32, pp. 295-298, 2005.

[26] P. Hallock and I. C. Benson, "Studies on the elastic properties of human isolated aorta," J. Clin. Invest., vol. 16, pp. 595-602, 1937.

[27] D. Seals, "Habitual exercise and the age-associated decline in large artery compliance.," *Exerc. Sport Sci. Rev.*, vol. 31, no. 2, pp. 68-72, 2003.

[28] J. van Lieshout and K. H. Wesseling, "Continuous cardiac output monitoring by pulse contour analysis?," *British Journal of Anaesthesia*, vol. 86, no. 4, pp. 467-468, 2001.

[29] M. Bourgeois, B. Gilbert, G. Bernuth, and E. Wood, "Continuous determination of beat-to-beat stroke volume from aortic pressure pulses in the dog," *Circ. Res.*, vol. 39, no. 1, pp. 15-24, 1976.

[30] D. Chemla, J.-L. Hebert, C. Coirault, K. Zamani, I. Suard, P. Colin, and Y. Lecarpentier, "Total arterial compliance estimated by stroke volume-to-aortic pressure pulse ratio in humans," *J. Appl. Physiol. Heart Circ. Physiol.*, pp. H500-H505, 1998.

[31] H. R. Warner, H. J. C. Swan, D. C. Connolly, R. G. Tompkins, and E. H. Wood, "Quantitation of beat-to-beat changes in stroke volume from the aortic pulse contour in man," *J Appl Physiol*, vol. 5, p. 495, 1953.

[32] J. R. M. Cundick and R. M. Gardner, "Clinical comparison of pressure-pulse and indicator-dilution cardiac output determination," *Circulation*, vol. 62, August 1980.

[33] Z. Liu, K. Brin, and F. Yin, "Estimation of total arterial compliance: an improved method and evaluation of current methods," *J. Appl. Physiol. Heart Circ. Physiol.*, pp. H588-H600, 1986.

[34] R. Burattini, R. Fogliardi, and K. Campbell, "Lumped model of terminal aortic impedance in the dog," *Annals of Biomedical Engineering*, vol. 22, pp. 381-391, 1994.

[35] N. Stergiopulos, B. E. Westerhof, and N. Westerhof, "Total arterial inertance as the fourth element of the windkessel model," *American Journal of Physiology*, pp. H81-H88, 1999.

[36] N. Stergiopulos, J.-J. Meister, and N. Westerhof, "Simple and accurate way for estimating total and segmental arterial compliance: the pulse pressure method," *Annals of Biomedical Engineering*, vol. 22, pp. 392-397, 1994.

[37] N. Stergiopulos, J.-J. Meister, and N. Westerhof, "Evaluation of methods for estimation of total arterial compliance," *J. Appl. Physiol. Heart Circ. Physiol.*, pp. H1540-H1548, 1995.

[38] W. Laskey, H. Parker, V. Ferrari, W. Kussmaul, and A. Noordegraaf, "Estimation of total systemic arterial compliance in humans," *J. Appl. Physiol.*, vol. 69, pp. 112-119, 1990.

[39] C. Quick, D. Berger, and A. Noordergraaf, "Apparent arterial compliance," *J. Appl. Physiol. Heart Circ. Physiol.*, vol. 274, pp. 1393-1403, 1998.

[40] G. Langewouters, K. Wesseling, and W. Goedhard, "The static elastic properties of 45 human thoracic and 20 abdominal aortas in vitro and the parameters of a new model," *J. Biomech.*, vol. 17, pp. 425-435, 1984.

[41] Y. Tardy, J.-J. Meister, F. Perret, H. Brunner, and M. Arditi, "Noninvasive estimate of the mechanical properties of peripheral arteries from ultrasonic and photoplethysmographic measurements," *Clin. Physiol. Physiological Meas.*, vol. 12, pp. 39-54, 1991.

[42] O. Godje, P. Lamm, C. Schmitz, M. Theil, and B. Reichart, "Continuous, less invasive, hemodynamic monitoring in intensive care after cardiac surgery," *Thoracic Cardiovascular Surgery*, vol. 46, pp. 242-249, 1998.

[43] D. Altman and J. Bland, "Measurement in medicine: the analysis of method comparsion studies," *The Statistician*, vol. 32, pp. 307-317, 1983.

[44] J. Bland and D. Altman, "Statistical methods for assessing agreement between two methods of clinical measurement," *Lancet*, vol. i, pp. 307-310, 1986.

What is claimed is:

1. A method for estimating beat-by-beat cardiovascular parameters and variables, comprising:
    processing two or more cycles of arterial blood pressure to determine a mean arterial blood pressure over each cycle beginning at a beat onset time and an inter-beat variability in blood pressure between the two or more cycles; and
    computing estimates of one or more cardiovascular parameters and variables from the mean arterial blood pressures, the inter-beat variability, and a beat-to-beat averaged Windkessel model of an arterial tree.

2. The method of claim 1, wherein the one or more cardiovascular parameters and variables include a beat-by-beat time constant of the arterial tree.

3. The method of claim 2, wherein the time constant is estimated over a data window.

4. The method of claim 2, wherein the time constant is estimated through optimization of an error criterion.

5. The method of claim 4, wherein the error criterion is least-squared error.

6. The method of claim 1, wherein the one or more cardiovascular parameters and variables include an uncalibrated beat-by-beat cardiac output.

7. The method of claim 6, further comprising computing calibrated beat-by-beat cardiac output from the uncalibrated beat-by-beat cardiac output using a calibration factor.

8. The method of claim 7, wherein the calibration factor is computed for each of the cycles.

9. The method of claim 7, wherein the calibration factor represents a lumped arterial compliance.

10. The method of claim 9, wherein the lumped arterial compliance is modeled as a function of mean arterial blood pressure.

11. The method of claim 9, wherein the lumped arterial compliance is modeled as a parameterized function of mean arterial blood pressure.

12. The method of claim 9, wherein the lumped arterial compliance is modeled as a two-parameter function of mean arterial blood pressure.

13. The method of claim 9, wherein the lumped arterial compliance is modeled as a constant.

14. The method of claim 11, 12 or 13, wherein a parameter of the lumped arterial compliance is estimated through optimization of an error criterion.

15. The method of claim 14, wherein the error criterion is least-squared error.

16. The method of claim 6, wherein the one or more cardiovascular parameters and variables include an uncalibrated beat-by-beat total peripheral resistance.

17. The method of claim 16, further comprising computing calibrated beat-by-beat total peripheral resistance from a ratio of the time constant to a lumped arterial compliance.

18. The method of claim 16, further comprising computing calibrated beat-by-beat total peripheral resistance from a ratio of mean arterial blood pressure to calibrated cardiac output.

19. The method of claim 16, further comprising computing calibrated beat-by-beat total peripheral resistance from a ratio of mean pressure to a systemic blood flow.

20. The method of claim 19, wherein the systemic blood flow is calculated as the calibrated cardiac output minus the product of lumped arterial compliance with a ratio of beat-to-beat arterial blood pressure change to beat duration.

21. The method of claim 1, wherein the arterial blood pressure is measured at a central artery of a cardiovascular system.

22. The method of claim 1, wherein the arterial blood pressure is measured at a peripheral artery of a cardiovascular system.

23. The method of claim 1, wherein the arterial blood pressure is measured using a noninvasive blood pressure device.

24. The method of claim 23, wherein the arterial blood pressure is measured using a photoplethysmographic blood pressure device.

25. The method of claim 23, wherein the arterial blood pressure is measured using a tonometric blood pressure device.

26. The method of claim 1, wherein processing the two or more cycles of arterial blood pressure includes obtaining a mean blood pressure, a diastolic blood pressure, and a systolic blood pressure for each cycle.

27. The method of claim 1, wherein processing the two or more cycles of arterial blood pressure includes obtaining the beat onset time for each cycle.

28. The method of claim 27, wherein processing the two or more cycles of arterial blood pressure includes computing a beat-to-beat arterial blood pressure change between consecutive beat onset times.

29. The method of claim 28, wherein processing the two or more cycles of arterial blood pressure includes estimating pulse pressure in each cycle as a proportionality constant multiplied by a difference between mean pressure and diastolic pressure in each cycle.

30. The method of claim 29, wherein the proportionality constant in each cycle is fixed.

31. The method of claim 1, wherein processing the two or more cycles of arterial blood pressure includes obtaining a beat duration for each cycle.

32. A system for estimating beat-to-beat cardiac output comprising:
    a blood pressure measuring device;
    a processor;
    a display;
    a user interface; and
    a memory storing computer executable instructions, which when executed by the processor cause the processor to:
    receive two or more cycles of arterial blood pressure from the blood pressure device;
    analyze the two or more cycles of arterial blood pressure to determine a mean arterial blood pressure over each cycle beginning at a beat onset time and an inter-beat variability in blood pressure between the two or more cycles;
    compute estimates of one or more cardiovascular system parameters and variables from the mean arterial blood pressures, the inter-beat variability, and a beat-to-beat averaged Windkessel model of an arterial tree; and
    display the estimates.

33. The system of claim 32, wherein the blood pressure measuring device is a noninvasive blood pressure measuring device.

34. The system of claim 33, wherein the noninvasive blood pressure measuring device is a photoplethysmographic blood pressure measuring device.

35. The system of claim 32, wherein the noninvasive blood pressure measuring device is a tonometric blood pressure measuring device.

36. The system of claim 32, wherein the arterial blood pressure is measured at a central artery of a cardiovascular system.

37. The system of claim 32, wherein the arterial blood pressure is measured at a peripheral artery of a cardiovascular system.

38. The system of claim 32, wherein the one or more cardiovascular parameters and variables include a beat-by-beat time constant of the arterial tree.

39. The system of claim 38, wherein the time constant is estimated over a data window.

40. The system of claim 38, wherein the time constant is estimated through optimization of an error criterion.

41. The system of claim 39, wherein the error criterion is least-squared error.

42. The system of claim 32, wherein the one or more cardiovascular parameters and variables include an uncalibrated beat-by-beat cardiac output.

43. The system of claim 32, further comprising computer executable instructions which, when executed by the processor, cause the processor to compute calibrated beat-by-beat cardiac output from the uncalibrated beat-by-beat cardiac output using a calibration factor.

44. The system of claim 43, further comprising computer executable instructions which, when executed by the processor, cause the processor to compute the calibration factor for each of the cycles.

45. The system of claim 43, wherein the calibration factor represents a lumped arterial compliance.

46. The system of claim 45, wherein the lumped arterial compliance is modeled as a function of mean arterial blood pressure.

47. The system of claim 45, wherein the lumped arterial compliance is modeled as a parameterized function of mean arterial blood pressure.

48. The system of claim 45, wherein the lumped arterial compliance is modeled as a two-parameter function of mean arterial blood pressure.

49. The system of claim 45, wherein the lumped arterial compliance is modeled as a constant.

50. The system of claim 47, 48, or 49, wherein a parameter of the lumped arterial compliance is estimated through optimization of an error criterion.

51. The system of claim 50, wherein the error criterion is least-squared error.

52. The system of claim 32, wherein the one or more cardiovascular parameters and variables include an uncalibrated beat-by-beat total peripheral resistance.

53. The system of claim 52, further comprising computer executable instructions which, when executed by processor, cause the processor to compute calibrated beat-by-beat total peripheral resistance from a ratio of the time constant to a lumped arterial compliance.

54. The system of claim 52, further comprising computer executable instructions which, when executed by the processor, cause the processor to compute calibrated beat-by-beat total peripheral resistance from a ratio of mean arterial blood pressure to calibrated cardiac output.

55. The system of claim 52, further comprising computer executable instructions which, when executed by the processor, cause the processor to compute calibrated beat-by-beat total peripheral resistance from a ratio of mean pressure to a systemic blood flow.

56. The system of claim 55, wherein the systemic blood flow is calibrated cardiac output minus the product of lumped arterial compliance with a ratio of beat-to-beat arterial blood pressure change to beat duration.

57. The system of claim 32, wherein analyzing the two or more cycles of arterial blood pressure includes obtaining a mean blood pressure, a diastolic blood pressure, and a systolic blood pressure for each cycle.

58. The system of claim 32, wherein analyzing the two or more cycles of arterial blood pressure includes obtaining the beat onset time for each cycle.

59. The system of claim 58, wherein analyzing the two or more cycles of arterial blood pressure includes computing a beat-to-beat arterial blood pressure change between consecutive beat onset times.

60. The system of claim 58, wherein analyzing the two or more cycles of arterial blood pressure includes estimating pulse pressure in each cycle as a proportionality constant multiplied by a difference between mean pressure and diastolic pressure in each cycle.

61. The system of claim 60, wherein the proportionality constant in each cycle is fixed.

62. The system of claim 32, wherein analyzing the two or more cycles of arterial blood pressure includes obtaining a beat duration for each cycle.

* * * * *